United States Patent
Matsumoto et al.

(10) Patent No.: US 12,402,238 B2
(45) Date of Patent: Aug. 26, 2025

(54) CONTROL METHOD FOR ACCELERATOR, CONTROL DEVICE FOR ACCELERATOR, AND PARTICLE-BEAM RADIATION TREATMENT SYSTEM

(71) Applicants: TOSHIBA ENERGY SYSTEMS & SOLUTIONS CORPORATION, Kawasaki (JP); KABUSHIKI KAISHA TOSHIBA, Tokyo (JP)

(72) Inventors: Munemichi Matsumoto, Fuchu (JP); Takuji Furukawa, Chiba (JP); Kota Mizushima, Chiba (JP); Katsushi Hanawa, Kita (JP)

(73) Assignees: TOSHIBA ENERGY SYSTEMS & SOLUTIONS CORPORATION, Kawasaki (JP); KABUSHIKI KAISHA TOSHIBA, Tokyo (JP)

( * ) Notice: Subject to any disclaimer, the term of this patent is extended or adjusted under 35 U.S.C. 154(b) by 1305 days.

(21) Appl. No.: 17/009,113

(22) Filed: Sep. 1, 2020

(65) Prior Publication Data

US 2020/0396824 A1 Dec. 17, 2020

Related U.S. Application Data

(63) Continuation of application No. PCT/JP2019/015257, filed on Apr. 8, 2019.

(30) Foreign Application Priority Data

Apr. 9, 2018 (JP) ................................. 2018-074908

(51) Int. Cl.
*H05H 7/04* (2006.01)
*A61N 5/10* (2006.01)
(Continued)

(52) U.S. Cl.
CPC ............. *H05H 7/04* (2013.01); *A61N 5/1077* (2013.01); *H05H 7/10* (2013.01); *H05H 13/04* (2013.01);
(Continued)

(58) Field of Classification Search
CPC . H05H 7/04; H05H 7/10; H05H 13/04; A61N 5/1077; A61N 2005/1087
See application file for complete search history.

(56) References Cited

U.S. PATENT DOCUMENTS 6,903,351 B1  6/2005 Akiyama et al.
7,982,198 B2  7/2011 Nishiuchi et al.
(Continued)

FOREIGN PATENT DOCUMENTS

CN  103083828 A   5/2013
CN  104582791 A * 4/2015 ............. A61N 5/103
(Continued)

OTHER PUBLICATIONS

International Search Report issued Jul. 2, 2019 in PCT/JP2019/015257 filed Apr. 8, 2019, 1 page.

*Primary Examiner* — Adam D Houston
(74) *Attorney, Agent, or Firm* — Oblon, McClelland, Maier & Neustadt, L.L.P.

(57) ABSTRACT

A control method for an accelerator according to the present embodiment is a control method for an accelerator that supplies a current generating a magnetic field to a plurality of deflection electromagnets based on a current-value instruction signal. The method includes providing a flat region that makes a current value of the deflection electromagnet constant in a case of an acceleration cycle involving emission of the charged particles, not providing the flat region in the current-value instruction signal in a case of an acceleration cycle, smoothing time change of a current value
(Continued)

in a transition of the current value to the flat region or a transition from the flat region, and determining a time required for the smoothing based on a predetermined energy for extracting the charged particles or a difference between energies before and after change to the predetermined extraction energy.

20 Claims, 14 Drawing Sheets

(51) Int. Cl.
    *H05H 7/10*     (2006.01)
    *H05H 13/04*     (2006.01)

(52) U.S. Cl.
    CPC ............ *A61N 2005/1087* (2013.01); *H05H 2007/046* (2013.01)

(56) References Cited

U.S. PATENT DOCUMENTS

| | | |
|---|---|---|
| 8,841,866 B2 | 9/2014 | Balakin |
| 9,215,791 B2 | 12/2015 | Arita et al. |
| 10,420,202 B2 * | 9/2019 | Matsumoto .............. H05H 7/02 |
| 2003/0057382 A1 | 3/2003 | Akiyama et al. |
| 2004/0069959 A1 | 4/2004 | Akiyama et al. |
| 2006/0231775 A1 * | 10/2006 | Harada .................... A61N 5/10 |
| | | 250/492.3 |
| 2010/0141183 A1 * | 6/2010 | Balakin .................. H05H 13/04 |
| | | 315/503 |
| 2012/0264998 A1 * | 10/2012 | Fujitaka ............... A61N 5/1043 |
| | | 600/1 |
| 2013/0193353 A1 * | 8/2013 | Ikeda ..................... H05H 13/04 |
| | | 315/503 |
| 2014/0152199 A1 | 6/2014 | Arita et al. |
| 2017/0339778 A1 * | 11/2017 | Aoki ...................... H05H 13/04 |
| 2018/0200534 A1 * | 7/2018 | Yamada ............... A61N 5/1071 |
| 2019/0255357 A1 * | 8/2019 | Takayama ................ A61N 2/06 |
| 2020/0128659 A1 * | 4/2020 | Hori ...................... H01F 7/0278 |

FOREIGN PATENT DOCUMENTS

| | | | | |
|---|---|---|---|---|
| CN | 105392527 B | * | 5/2018 | ........... A61N 5/1064 |
| CN | 115299183 A | * | 11/2022 | ........... A61N 5/1075 |
| CN | 112166651 B | * | 9/2023 | ............... A61N 5/10 |
| JP | H0992499 A | * | 4/1997 | |
| JP | H09223600 A | * | 8/1997 | |
| JP | H10118204 A | * | 5/1998 | |
| JP | H10199700 A | * | 5/1998 | |
| JP | 2000162391 A | * | 6/2000 | |
| JP | 2006026422 A | * | 2/2006 | ........... A61N 5/1042 |
| JP | 2008-226740 A | | 9/2008 | |
| JP | 2010201099 A | * | 9/2010 | |
| JP | 2010238463 A | * | 10/2010 | |
| JP | 2011129353 A | * | 6/2011 | |
| JP | 2011198748 A | * | 10/2011 | |
| JP | 4873563 B2 | | 2/2012 | |
| JP | 2014-110168 A | | 6/2014 | |
| JP | 2015028876 A | * | 2/2015 | |
| JP | 2016-103357 A | | 6/2016 | |
| JP | 6037675 B2 | | 12/2016 | |
| JP | 2017-112021 A | | 6/2017 | |
| JP | 2018114127 A | * | 7/2018 | ............. A61N 5/103 |
| SG | 189670 A1 | | 5/2013 | |
| WO | WO 01/24591 A1 | | 4/2001 | |
| WO | WO-2013069090 A1 | * | 5/2013 | ........... A61N 5/1042 |
| WO | WO-2021260988 A1 | * | 12/2021 | ........... A61N 5/1078 |

\* cited by examiner

| ENERGY No. | NUMBER OF CLOCKS WHEN CLOCK IS STOPPED | NUMBER OF SMOOTHING CLOCKS |
|---|---|---|
| 1 | 1520 | 100 |
| 2 | 1530 | 80 |
| 3 | 1540 | 60 |
| 4 | 1550 | 60 |
| ... | | |
| 998 | 11490 | 40 |
| 999 | 11500 | 40 |
| 1000 | 11510 | 20 |

| NUMBER OF CLOCKS FROM START OF SMOOTHING | CLOCK INTERVAL [μs] (ENERGY No. 4) | CLOCK INTERVAL [μs] (ENERGY No. N) |
|---:|---:|---:|
| 0 | 10 | 10 |
| 1 | 12 | 11 |
| 2 | 16 | 13 |
| 3 | 22 | 16 |
| 4 | 30 | 20 |
| 5 | 40 | 25 |
| 6 | 52 | 31 |
| 7 | 66 | 38 |
| 8 | 82 | 46 |
| 9 | 100 | 55 |
| 10 | 120 | 65 |
| 11 | 142 | 76 |
| ... | ... | ... |
| 96 | 9322 | 4666 |
| 97 | 9516 | 4763 |
| 98 | 9712 | 4861 |
| 99 | 9910 | 4960 |
| 100 | 10110 | 5060 |

FIG. 10

| NUMBER OF CLOCKS FROM START OF SMOOTHING | TABLE OF CLOCK OUTPUT TIME FROM START OF SMOOTHING [μs] (ENERGY No. 4) | TABLE OF CLOCK OUTPUT TIME FROM START OF SMOOTHING [μs] (ENERGY No. N) |
|---|---|---|
| 0 | 0 | 0 |
| 1 | 12 | 11 |
| 2 | 28 | 24 |
| 3 | 50 | 40 |
| 4 | 80 | 60 |
| 5 | 120 | 85 |
| 6 | 172 | 116 |
| 7 | 238 | 154 |
| 8 | 320 | 200 |
| 9 | 420 | 255 |
| 10 | 540 | 320 |
| 11 | 682 | 396 |
| ... | ... | ... |
| 96 | 305152 | 153056 |
| 97 | 314668 | 157819 |
| 98 | 324380 | 162680 |
| 99 | 334290 | 167640 |
| 100 | 344400 | 172700 |

FIG. 12

CONTROL METHOD FOR ACCELERATOR, CONTROL DEVICE FOR ACCELERATOR, AND PARTICLE-BEAM RADIATION TREATMENT SYSTEM

CROSS-REFERENCE TO RELATED APPLICATIONS

This application is a continuation application of International Application No. PCT/JP2019/015257, filed Apr. 8, 2019, which claims priority to Japanese Patent Application No. 2018-074908 filed Apr. 9, 2018. The contents of these applications are incorporated herein by reference in their entirety.

FIELD

An embodiment of the present invention relates to a control method for an accelerator, a control device for an accelerator, and a particle-beam radiation treatment system.

BACKGROUND

In general, an accelerator used in a particle-beam radiation treatment system injects charged particles accelerated from an ion source by an injector into a main accelerator at an injection energy, and accelerates the particles by the main accelerator to a target energy. The charged particles are caused to revolve along a predetermined orbit by a magnetic field generated by a deflection electromagnet in the main accelerator. The charged particles are accelerated along the predetermined orbit by increasing a current supplied from a power supply of the deflection electromagnet to increase the magnetic field strength and supplying high-frequency power having a frequency corresponding to the magnetic field strength to a high-frequency accelerating cavity at the same time.

When the charged particles are extracted from the main accelerator, acceleration is performed to a predetermined energy, and deceleration to a constant energy is then performed, and thereafter the charged particles are extracted from the main accelerator while the energy of the charged particles is kept constant. The charged particles thus extracted are introduced into a treatment room through a beam transport system. In addition, in this method, after completion of irradiation at the predetermined energy, deceleration to the next different energy is performed, and the charged particles are extracted again while the energy of the charged particles is kept constant.

In order to maintain the charged particles to be constant in a predetermined energy state during deceleration, it is necessary to change a current value of the deflection electromagnet and the frequency of the high-frequency power corresponding thereto from decrease change to constant values. However, when the current of the deflection electromagnet is abruptly changed to a constant value during decrease change, a current response is not performed in time, and thus a current deviation becomes large and a position jump of charged particles or elimination of charged particles occurs. Therefore, before and after the current value of the deflection electromagnet is changed to a constant value, a smoothing region is provided to achieve smooth transition of the current to the constant value.

In conventional accelerator control, current control for a deflection electromagnet that achieves the above operation method employs a method in which a current-value instruction signal (a current signal) with respect to a time axis calculated in advance is stored in a memory and is output to a power supply of the deflection electromagnet successively. In this case, a short and flat region in which a current value is constant is provided in a portion corresponding to a predetermined extraction energy. As described above, the short and flat region and the smoothing regions in front and behind the short and flat region are incorporated in an instruction pattern of the current-value instruction signal. The energy is kept constant by stopping updating output of the current value at a timing at which the current value of the deflection electromagnet enters this short and flat region and by retaining the current value.

The number of types of energies for extracting charged particles achieved in a conventional accelerator is about ten, and further subdivided types of energies are generated by using a hardware device, such as a range shifter. Meanwhile, switching a range shifter or the like requires time, and maintenance of the hardware or the like is also required. Therefore, it is demanded to generate the subdivided types of energies for extracting charged particles only by an accelerator. On the other hand, it is demanded to shorten an acceleration cycle in order to shorten a treatment time.

BRIEF DESCRIPTION OF THE DRAWINGS

FIG. 10 is a diagram representing a relation between the number of clocks from start of smoothing and a clock interval.

FIG. 12 is a diagram representing a relation between the number of clocks from start of smoothing and an elapsed time.

DETAILED DESCRIPTION

Figure 1:
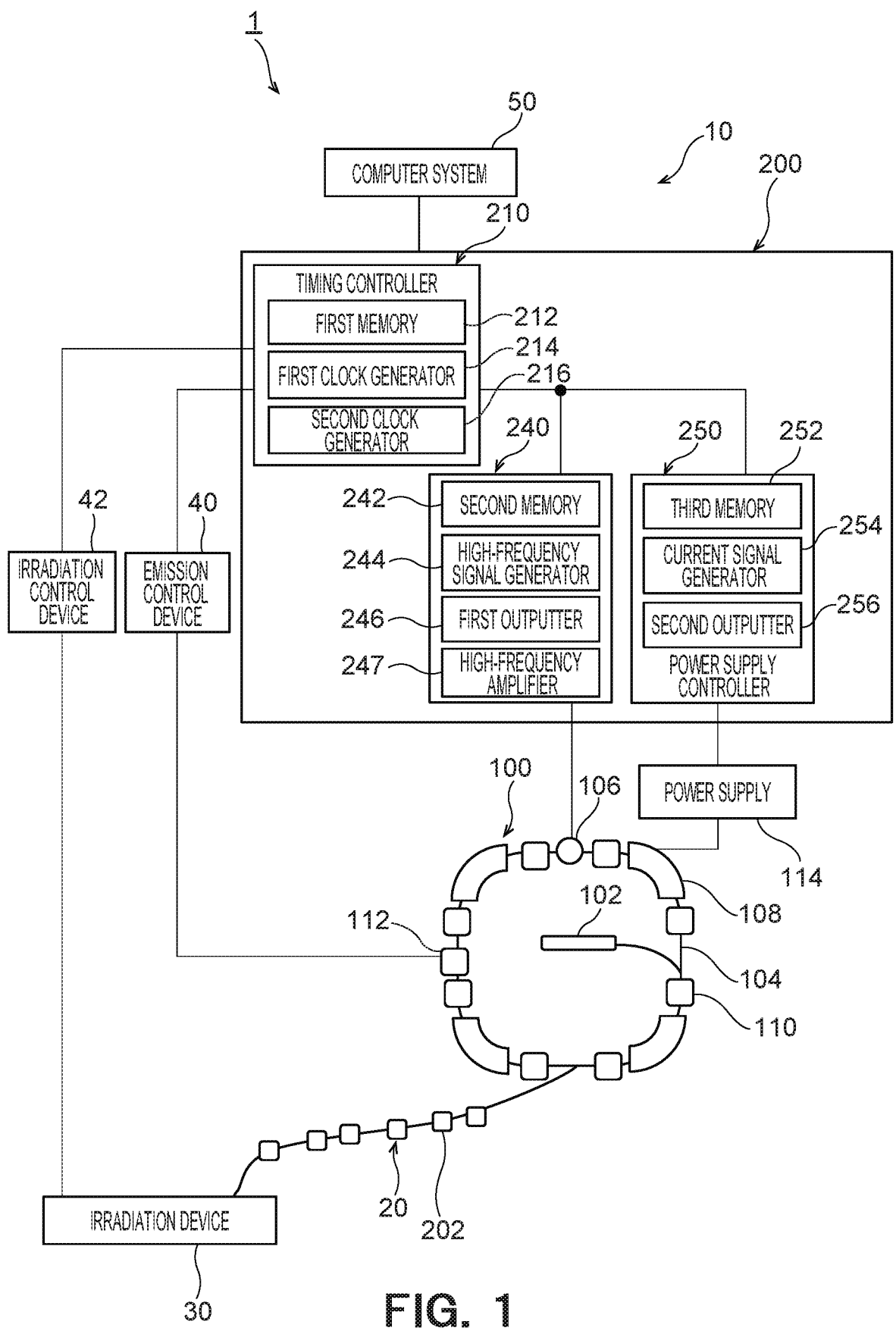
FIG. 1 is a diagram illustrating a schematic overall configuration of a particle-beam radiation treatment system 1 according to a first embodiment.

A control method for an accelerator according to the present embodiment is a control method for an accelerator including a plurality of deflection electromagnets configured to generate a magnetic field that causes charged particles to revolve in a main accelerator in accordance with an acceleration energy of the charged particles and a power supply configured to supply a current that generates the magnetic field to the deflection electromagnets based on a current-value instruction signal, the method comprising: providing a flat region that makes a current value of the deflection electromagnet constant to correspond to a predetermined energy for extracting the charged particles in the current-value instruction signal in a case of an acceleration cycle involving emission of the charged particles to a beam transport system; not providing the flat region in the current-value instruction signal in a case of an acceleration cycle not involving emission of the charged particles to the beam transport system; smoothing time change of a current value of the deflection electromagnet in a transition of the current value to the flat region or a transition from the flat region; and determining a time required for the smoothing based on a predetermined energy for extracting the charged particles or a difference between energies before and after change to the predetermined extraction energy.

A control method for an accelerator according to the present embodiment is a control method for an accelerator including an injector configured to accelerate charged particles to an injection energy and inject the charged particles into a main accelerator, a high-frequency acceleration cavity configured to give an acceleration energy to the charged particles injected into the main accelerator, a plurality of deflection electromagnets configured to generate a magnetic field that causes the charged particles to revolve in the main accelerator in accordance with the acceleration energy of the charged particles, a power supply configured to supply a current that generates the magnetic field to the deflection electromagnets based on a current-value instruction signal, and an emission device for causing the charged particles to be emitted from the main accelerator to a beam transport system, the method comprising: generating a flat bottom section corresponding to a lowest energy of the charged particles, a top point or a flat top section corresponding to a highest energy, an acceleration section for acceleration from the flat bottom section, and a deceleration section for deceleration from the top point or the flat top section to the flat bottom in time change of a current value of the deflection electromagnet in an acceleration cycle not involving emission of the charged particles to the beam transport system, and not generating a flat region that makes the current value of the deflection electromagnet constant to correspond to a predetermined extraction energy; generating, in time change of the current value of the deflection electromagnet in an acceleration cycle involving emission of the charged particles to the beam transport system, the flat region in which the current value is constant to correspond to a predetermined extraction energy in a middle of a section corresponding to at least either the deceleration section or the acceleration section; and smoothing the time change of the current value in a transition from the corresponding section to the flat region or a transition from the flat region to the corresponding section, and determining a time required for the smoothing based on a predetermined energy for extracting the charged particles or a difference between energies before and after change to the predetermined extraction energy.

A control device for an accelerator according to the present embodiment is a control device for an accelerator including a plurality of deflection electromagnets configured to generate a magnetic field that causes charged particles to revolve in a main accelerator in accordance with an acceleration energy of the charged particles and a power supply configured to supply a current that generates the magnetic field to the deflection electromagnets based on a current-value instruction signal, the device comprising a current signal generator configured to generate the current-value instruction signal provided with a flat region that makes a current value of the deflection electromagnet constant to correspond to a predetermined energy for extracting the charged particles in a case of an acceleration cycle involving emission of the charged particles to a beam transport system, and generate the current-value instruction signal not provided with the flat region in a case of an acceleration cycle not involving emission of the charged particles to the beam transport system, wherein the current-value instruction signal includes a smoothing section in which current change is made smooth in a transition of the current value of the deflection electromagnet to the flat region or a transition from the flat region, and a length of time of the smoothing section is determined based on a predetermined energy for extracting the charged particles or a difference between energies before and after change to the predetermined extraction energy.

A particle-beam radiation treatment system according to the present embodiment is a particle-beam radiation treatment system, comprising: an injector configured to accelerate charged particles to an injection energy and inject the charged particles to a main accelerator; a high-frequency acceleration cavity configured to give an acceleration energy to the charged particles injected into the main accelerator; a plurality of deflection electromagnets configured to generate a magnetic field that causes the charged particles to revolve in the main accelerator in accordance with the acceleration energy of the charged particles; a power supply configured to supply a current that generates the magnetic field to the deflection electromagnets based on a current-value instruction signal; an emission device for causing the charged particles to be emitted from the main accelerator to a beam transport system; and a control device configured to control at least the power supply among the injector, the high-frequency acceleration cavity, the power supply, and the emission device, wherein the control device includes a current signal generator configured to generate the current-value instruction signal provided with a flat region that makes a current value of the deflection electromagnet constant to correspond to a predetermined energy for extracting the charged particles in a case of an acceleration cycle involving emission of the charged particles to the beam transport system, generate the current-value instruction signal not provided with the flat region in a case of an acceleration cycle not involving emission of the charged particles to the beam transport system, generate a smoothing section that smoothes current change in a transition to the flat region or a transition from the flat region, and determine a length of time of the smoothing section based on a predetermined energy for extracting the charged particles or a difference between energies before and after change to the predetermined extraction energy.

A particle-beam radiation treatment system according to embodiments of the present invention will now be explained in detail with reference to the accompanying drawings. The embodiments described below are only examples of the embodiments of the present invention and it is not to be understood that the present invention is limited to these embodiments. In the drawings referred to in the embodiments, same parts or parts having identical functions are denoted by like or similar reference characters and there is a case where redundant explanations thereof are omitted. Further, for convenience of explanation, there are cases where dimensional ratios of the parts in the drawings are different from those of actual products and some part of configurations is omitted from the drawings.

First Embodiment

First, an overall configuration of a particle-beam radiation treatment system 1 is described with reference to FIG. 1. FIG. 1 is a diagram illustrating a schematic overall configuration of the particle-beam radiation treatment system 1 according to a first embodiment. As illustrated in FIG. 1, the particle-beam radiation treatment system 1 is a system that irradiates charged particles, such as carbon ions, to an affected area of a patient to perform medical treatment. More specifically, this particle-beam radiation treatment system 1 is configured to include an accelerator system 10, a beam transport system 20, an irradiation device 30, an irradiation control device 42, an emission control device 40, and a computer system 50.

The computer system 50 is configured by a PC and a server, and generates parameters for various control devices from data, for example, a treatment plan retained therein and sets the parameters. Each control device is configured by a high-performance CPU or FPGA and executes control in such a manner that various devices operate in accordance with the set parameters.

The accelerator system 10 accelerates charged particles. The accelerator system 10 is configured to include an accelerator 100 and a control device 200. The accelerator 100 is configured to include an injector 102, a main accelerator 104, a high-frequency acceleration cavity 106, a plurality of deflection electromagnets 108, a plurality of quadrupole electromagnets 110, and an emission device 112.

The injector 102 is connected to the main accelerator 104. The injector 102 is, for example, a linac, and accelerates charged particles of generated protons, helium, carbon, nitrogen, oxygen, neon, silicon, argon, or the like to an injection energy and supplies the charged particles to the main accelerator 104.

The injector 102 is connected to the main accelerator 104 and charged particles are injected from the injector 102. The main accelerator 104 is, for example, a synchrotron and has an annular vacuum duct. Accordingly, the charged particles injected from the injector 102 revolve in a predetermined orbit in the duct of the main accelerator 104. That is, the high-frequency acceleration cavity 106, the deflection electromagnets 108, and the quadrupole electromagnets 110 are arranged along the annular vacuum duct in the main accelerator 104.

The high-frequency acceleration cavity 106 applies a high-frequency voltage to the inside of the high-frequency acceleration cavity 106 to accelerate the charged particles revolving in the duct of the main accelerator 104. The high-frequency acceleration cavity 106 accelerates the charged particles revolving on the orbit by an electric field generated across electrodes provided therein. In this manner, the high-frequency acceleration cavity 106 accelerates or decelerates the charged particles revolving in the main accelerator 104 to a plurality of stationary energies that are in accordance with energies of the charged particles to be irradiated to a patient.

The deflection electromagnet 108 generates a magnetic field that is in accordance with an acceleration energy of the charged particles revolving in the main accelerator 104. The magnetic field generated by the deflection electromagnet 108 acts on the charged particles to cause the charged particles to revolve along the predetermined orbit in the main accelerator 104. Further, a magnetic field generated by the quadrupole electromagnet 110 acts on the charged particles revolving in the main accelerator 104 to converge or disperse the charged particles. That is, the deflection electromagnets 108 and the quadrupole electromagnets 110 are synchronized with acceleration or deceleration of the charged particles in the high-frequency acceleration cavity 106, and are controlled to generate magnetic fields having the strengths that are in accordance with the energy of the charged particles that have been accelerated or decelerated.

The emission device 112 applies a high-frequency electric field in a direction perpendicular to a traveling direction of charged particles to widen the width of a beam of charged particles revolving in the accelerator 100. Accordingly, particles of the beam of charged particles which have been placed on a resonance region from a stable region are directed to an emission orbit and are emitted to the beam transport system 20. The emission device 112 controls emission and stop of emission of charged particles to the beam transport system 20 by changing the strength of the electric field.

A power supply 114 supplies power supplied from a power system to the deflection electromagnets 108 and the quadrupole electromagnets 110. In more detail, the power supply 114 supplies, based on a time-series current signal generated by the control device 200, currents for generating magnetic fields corresponding to the energy of charged particles to the deflection electromagnets 108 and the quadrupole electromagnets 110.

The control device 200 controls the entire particle-beam radiation treatment system 1. Detailed configurations of the control device 200 will be described later.

The irradiation device 30 is provided on a structure, such as a wall of a treatment room, or in a rotating gantry, for example, and irradiates charged particles transported by the beam transport system 20 to a patient. When passing through the body of a patient, the charged particles lose kinetic energy, stop, and release high energy called a Bragg peak near a stop position. Therefore, by aligning the stop position of the charged particles with an affected area of the patient's charged particles, it is possible to damage cells in the affected area, for example, cancer cells while reducing influences on a healthy tissue.

The emission control device 40 controls the emission device 112 to perform emission and stop of emission of charged particles to the beam transport system 20 based on a signal requesting a beam of charged particles from the irradiation control device 42.

Next, the detailed configurations of the control device 200 are described. As illustrated in FIG. 1, the control device 200 includes a timing controller 210, a high-frequency acceleration cavity controller 240, and a power supply controller 250.

The timing controller 210 executes timing control for the high-frequency acceleration cavity controller 240 and the power supply controller 250. More specifically, the timing controller 210 is configured to include a first memory 212, a first clock generator 214, and a second clock generator 216. The first memory 212 stores therein a condition for stopping a clock signal and a condition for releasing the clock signal, for example, determined based on the energy of charged particles to be irradiated to a patient 400. The energy of the charged particles to be irradiated to the patient 400 is output from the irradiation control device 42. The second clock generator 216 according to the present embodiment corresponds to a clock signal generator.

The first clock generator 214 generates a reference clock signal that is an internal clock for measuring time and has a frequency of 10 MHz (a period of 100 ns), for example. This first clock generator 214 has a clock generation circuit, for example.

The second clock generator 216 generates a clock signal for control that is synchronized with the reference clock signal generated by the first clock generator 214. The period of the clock signal is, for example, 100 kHz (10 μs). The second clock generator 216 has a clock generation circuit, for example.

The second clock generator 216 outputs a reset signal to the high-frequency acceleration cavity controller 240 and the power supply controller 250. Accordingly, the high-frequency acceleration cavity controller 240 and the power supply controller 250 start control synchronized with the clock signal generated by the second clock generator 216.

The irradiation control device 42 outputs an irradiation request signal to the emission control device 40 to request emission of a beam of charged particles. Specifically, the irradiation control device 42 outputs a signal of the energy of charged particles to be irradiated to the patient 400 and a request signal that requests emission of a beam of charged particles from the accelerator 100 in order to actually irradiate the beam of charged particles to the patient 400. The irradiation control device 42 also controls scanning of the beam of charged particles to be irradiated to a patient.

The high-frequency acceleration cavity controller 240 controls the frequency and the amplitude of a high-frequency electric field to be applied to electrodes of the high-frequency acceleration cavity 106. In more detail, the high-frequency acceleration cavity controller 240 is configured to include a second memory 242, a high-frequency signal generator 244, a first outputter 246, and a high-frequency amplifier 247. The second memory 242 stores therein a frequency reference signal and an amplitude reference signal that are associated with times-series numbers.

The high-frequency signal generator 244 generates a high-frequency signal by using the frequency reference signal and the amplitude reference signal stored in the second memory 242 in response to reception of the clock signal generated by the second clock generator 216, and sequentially outputs the high-frequency signal to the first outputter 246. Further, when the clock of the second clock generator 216 stops, the high-frequency signal generator 244 continues to output the high-frequency signal that is being output.

The first outputter 246 generates a sign-wave instruction signal based on the high-frequency signal generated by the high-frequency signal generator 244, and outputs the sign-wave instruction signal to the high-frequency acceleration cavity 106 via the high-frequency amplifier 247 that amplifies the sign-wave instruction signal. Accordingly, the high-frequency acceleration cavity 106 generates a high-frequency electric field to be applied to electrodes thereof based on these high-frequency signals.

The power supply controller 250 controls a current that the power supply 114 supplies to the deflection electromagnet 108. More specifically, the power supply controller 250 is configured to include a third memory 252, a current signal generator 254, and a second outputter 256.

The third memory 252 is a pattern memory that stores therein a current reference signal associated with consecutive numbers, for example. Instruction values of the reference signal correspond to values of a current that the power supply 114 supplies to the deflection electromagnet 108. Further, the current reference signal and a reference signal used for controlling the high-frequency acceleration cavity 106 are associated with each other in such a manner that charged particles to be accelerated revolve in a predetermined orbit. Accordingly, the charged particles revolve in the predetermined orbit.

In a case of an acceleration cycle involving emission of charged particles to the beam transport system 20, the current signal generator 254 generates a current signal that is provided with a flat region that makes a current value of the deflection electromagnet 108 constant to correspond to a predetermined energy for extracting the charged particles. In a case of an acceleration cycle not involving emission of charged particles to the beam transport system 20, the current signal generator 254 generates a current signal that is not provided with the flat region. The current signal generator 254 outputs the current reference signal stored in the third memory 252 as the current signal to the second outputter 256 sequentially in response to reception of the clock signal generated by the second clock generator 216. Further, when the clock of the second clock generator 216 stops, the current signal generator 254 continues to output the current signal that is being output. More detailed configurations of the current signal generator 254 will be described later.

The second outputter 256 outputs the current signal generated by the current signal generator 254 to the power supply 114. Accordingly, the power supply 114 generates a current that is caused to flow in the deflection electromagnet 108 based on this current signal. The first memory 212, the second memory 242, and the third memory 252 according to the present embodiment correspond to a memory, and the second outputter 256 according to the present embodiment corresponds to an outputter.

Next, an example of generation of a current signal in the current signal generator 254 is described in detail with reference to FIGS. 2 to 7. First, smoothing of a current instruction signal is described with reference to FIG. 5. In front and behind the flat region described above, a smoothing region (a smoothing section) is formed in such a manner that a current in the deflection electromagnet 108 is made smooth within a range in which the current can respond. In a case where a current response in the deflection electromagnet 108 with respect to an instruction value of a current signal is not in time, a position jump or elimination of charged particles may occur. However, it is possible to avoid occurrence of the position jump and elimination by smoothing.

Figure 2:
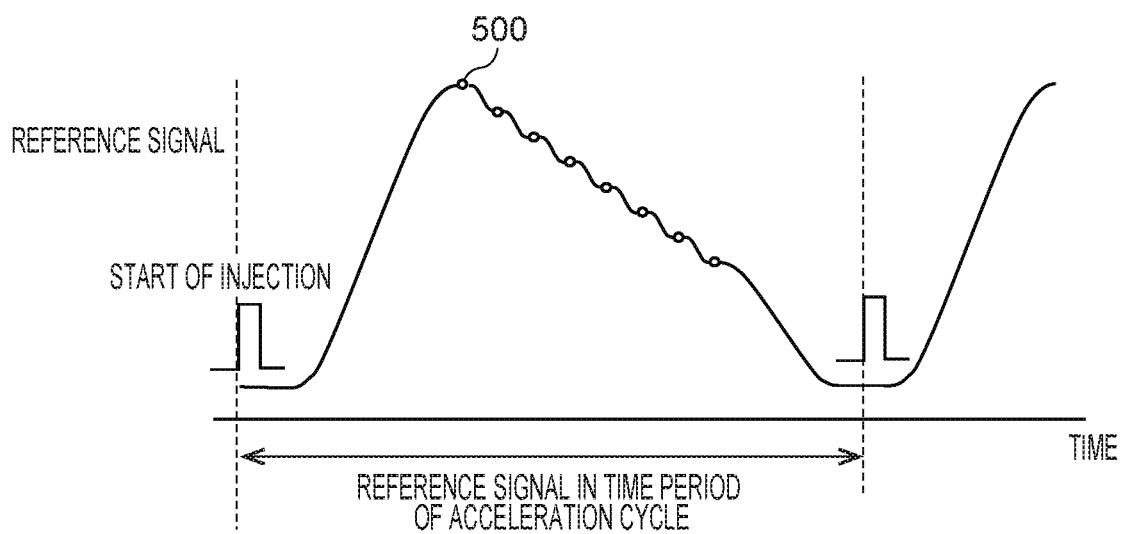
FIG. 2 is a diagram exemplifying a current reference signal in a time period of an acceleration cycle.

Next, an example of a current reference signal in a time period of an acceleration cycle is described with reference to FIG. 2. In FIG. 2, the horizontal axis represents a time, and the vertical axis represents a reference signal. An acceleration cycle means a time period from injection of charged particles from the injector 102 to the next injection of charged particles from the injector 102. In the acceleration cycle, the charged particles are accelerated from a flat bottom energy to a top energy and are decelerated to the original flat bottom energy.

In FIG. 2, a plurality of stop points 500 denote points at which a clock signal generated by the second clock generator 216 can be stopped. Each stop point 500 corresponds to a stationary energy of charged particles revolving in the main accelerator 104. Further, smoothing regions are formed in front and behind each stop point 500, respectively.

Figure 3:
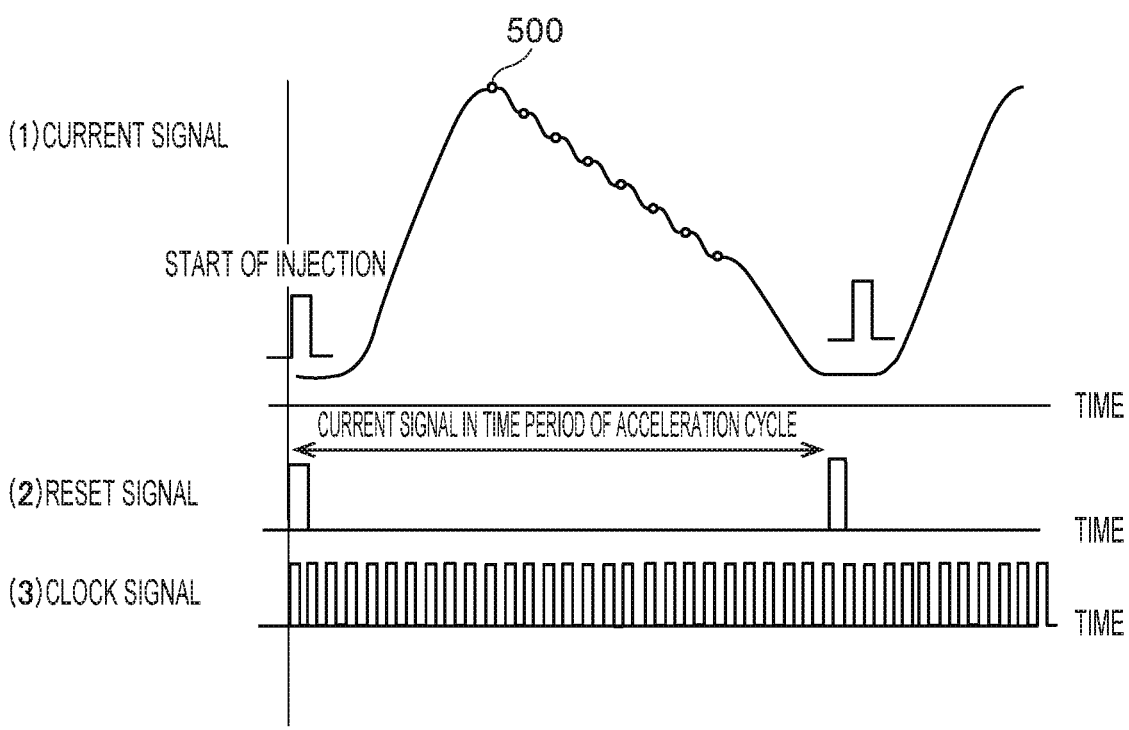
FIG. 3 is a diagram representing a relation between a current signal generated based on the reference signal illustrated in FIG. 2 and a clock signal.

FIG. 3 is a diagram illustrating a current signal generated based on the reference signal illustrated in FIG. 2, that is, a relation between the current signal and a clock signal. The horizontal axis represents a time, and the vertical axis represents an instruction value of the current signal, that is, a current value in (1), a reset signal in (2), and the clock signal in (3). As the current signal illustrated in FIG. 3, a signal equivalent to a current reference signal is output, because the clock signal generated by the second clock generator 216 has never been stopped. The current signal according to the present embodiment corresponds to a current-value instruction signal.

Figure 4:
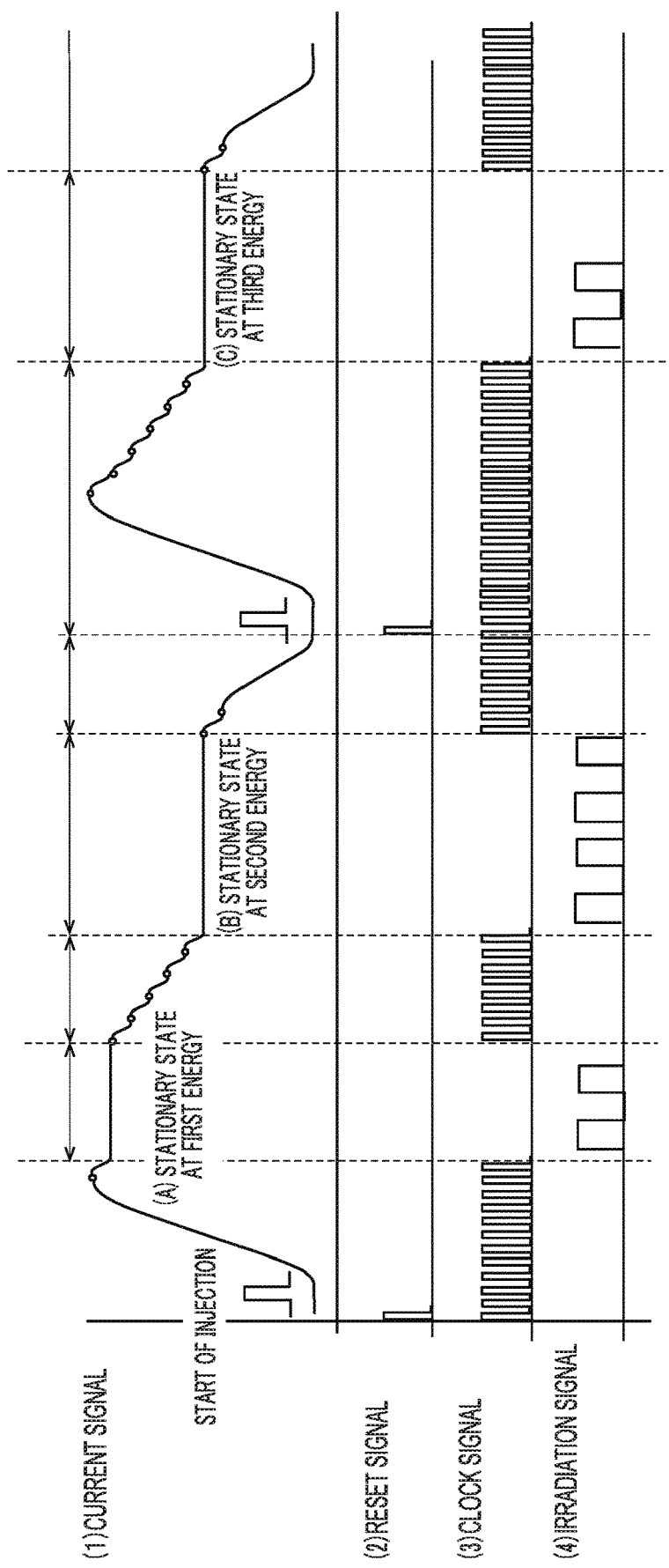
FIG. 4 is a diagram illustrating a current signal generated when a clock signal is stopped.
Figure 5:
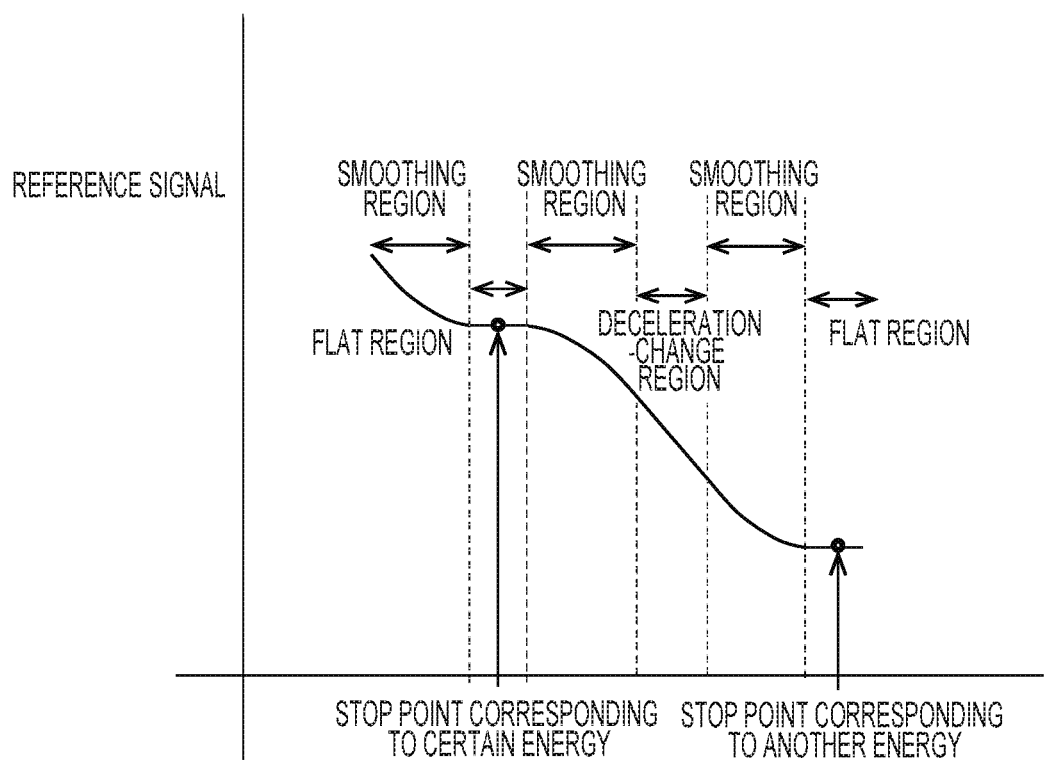
FIG. 5 is an enlarged view of a part of a reference signal.

FIG. 4 is a diagram illustrating a relation between a current signal generated based on a reference signal when a clock signal is stopped, and the clock signal. The horizontal axis represents a time, and the vertical axis represents an instruction value of the current signal, that is, a current value in (1), a reset signal in (2), the clock signal in (3), and an irradiation signal in (4). The irradiation signal is output by the irradiation control device 42 in order to irradiate a beam of charged particles to a patient. In accordance with this irradiation signal, charged particles are emitted from the accelerator 100 to the beam transport system 20.

As illustrated in FIG. 4, the second clock generator 216 stops outputting the clock signal when the number of clocks reaches the number corresponding to a predetermined stop point based on a stop condition stored in the first memory. The current signal generator 254 outputs a reference signal corresponding to the time at which the clock signal is stopped, as the current signal continuously. Although a stop point is set in a process of decelerating charged particles in the example of FIG. 3, the stop point may be set in a process of accelerating the charged particles.

The stop condition is an energy of charged particles to be irradiated to the patient 400 and is stored based on a signal output from the irradiation control device 42 or settings from the computer system 50.

In a case of the reference signal in which the stop points 500 and smoothing regions are provided for respective energies for extracting charged particles in this manner, an acceleration cycle becomes longer in proportion to the number of beam extraction energies, resulting in increase of a treatment time.

Figure 6:
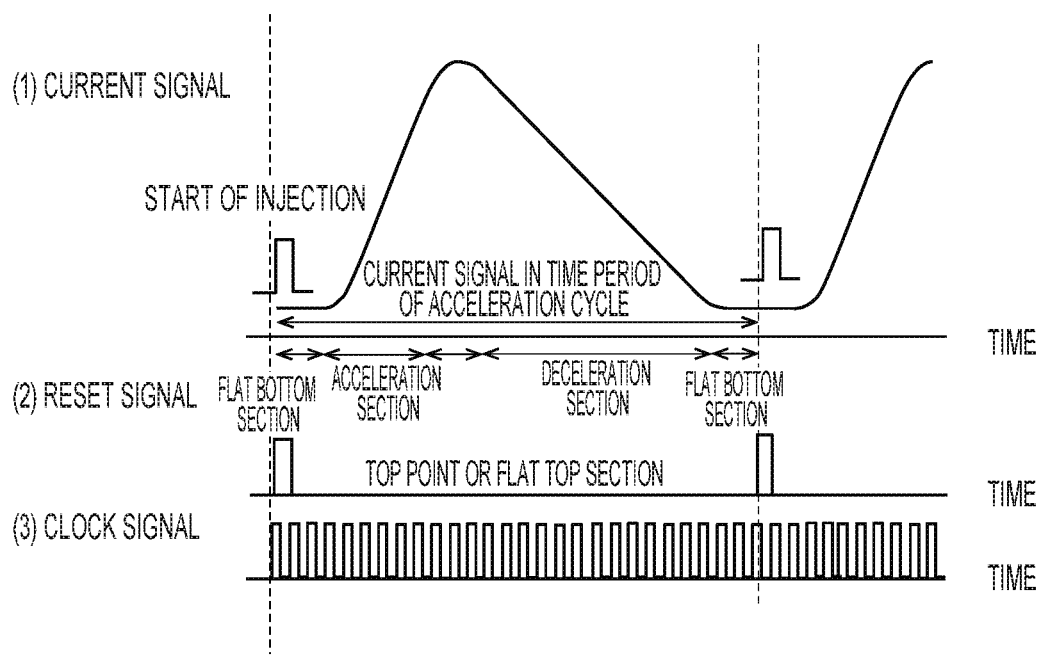
FIG. 6 is a diagram exemplifying a current signal output based on a reference signal.

Here, a reference signal not provided with a region corresponding to a smoothing region is described with reference to FIG. 6. FIG. 6 is a diagram exemplifying a current signal output based on a reference signal according to the present embodiment in an acceleration cycle. The horizontal axis represents a time, and the vertical axis represents an instruction value of the current signal, that is, a current value in (1), a reset signal in (2), and a clock signal in (3).

The instruction value of the current signal in (1) of FIG. 6 indicates an equivalent value to an instruction value of the reference signal because the clock signal is not stopped. This time-series reference signal is stored in advance in the third memory 252 (FIG. 1).

As illustrated in FIG. 6, this reference signal is not provided with a smoothing region, and thus a time period of an acceleration cycle is shorter than in a case where the smoothing region is provided. Time change of the current value in the acceleration cycle includes a flat bottom section corresponding to the lowest energy, a top point or a flat top section corresponding to the highest energy, an acceleration section for acceleration from the flat bottom section, and a deceleration section for deceleration from the top point or the flat top section to the flat bottom section.

Next, a clock signal output by the second clock generator 216 (FIG. 1) and a current signal generated by the current signal generator 254 (FIG. 1) according to the present embodiment are described with reference to FIG. 7.

Figure 7:
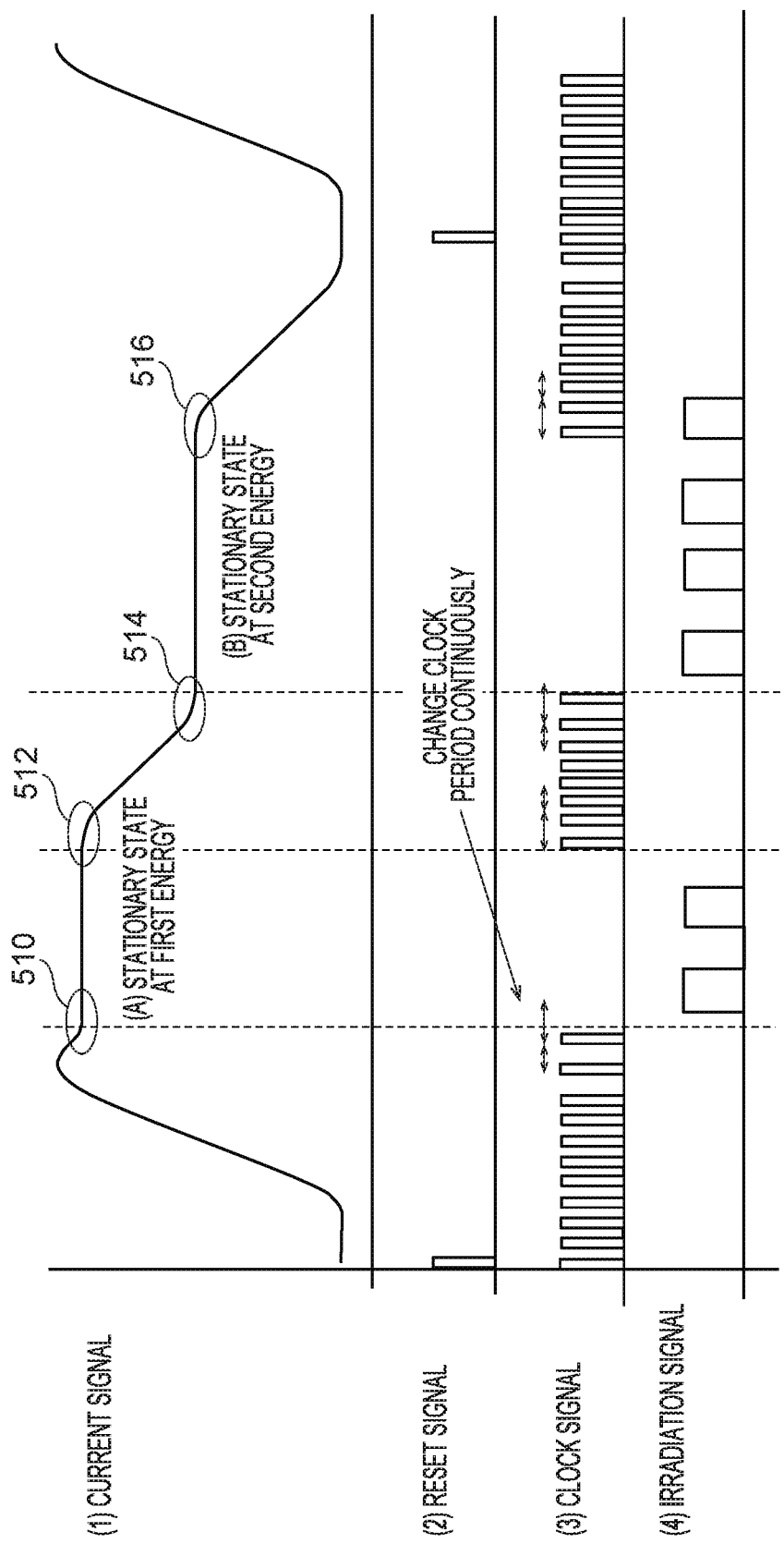
FIG. 7 is a time chart for explaining a clock signal and a current signal.

FIG. 7 is a time chart for explaining the clock signal output by the second clock generator 216 (FIG. 1) and the current signal generated by the current signal generator 254 (FIG. 1) according to the present embodiment. The horizontal axis represents a time, and the vertical axis represents an instruction value of the current signal, that is, a current value in (1), a reset signal in (2), the clock signal in (3), and an irradiation signal in (4).

As illustrated in FIG. 7, the second clock generator 216 (FIG. 1) according to the present embodiment continuously changes the period of the clock signal before and after the energy of charged particles enters a stationary state. That is, the second clock generator 216 continuously changes the period of the clock signal corresponding to a smoothing region. The period of the clock signal corresponding to the smoothing region is calculated in advance based on transient characteristics of a current in the deflection electromagnet 108. That is, the second clock generator 216 makes change of the current flowing in the deflection electromagnet 108 with respect to time smaller than a predetermined value by providing a time-series smoothing section in which the clock period is continuously increased or decreased. Here, smoothing a current means to make change of a current flowing in the deflection electromagnet 108 with respect to time smaller than a predetermined value.

The current signal generator 254 (FIG. 1) according to the present embodiment sequentially outputs a reference signal (for example, FIG. 6) stored in the third memory 252 in response to the clock signal output by the second clock generator 216. Accordingly, smoothing regions 510 to 516 and the like are generated in the current signal.

As described above, in time change of a current value of the deflection electromagnet 108 in a cycle of accelerating charged particles, a flat bottom section corresponding to the lowest energy, a top point or a flat top section corresponding to the highest energy, an acceleration section for acceleration from the flat bottom, and a deceleration section for deceleration from the flat top to the flat bottom are provided.

Meanwhile, in time change of the current of the deflection electromagnet 108 in an acceleration cycle involving emission of charged particles to the beam transport system 20, a flat region is provided which is for making a current value corresponding to a predetermined extraction energy constant in the middle of at least either the deceleration section or the acceleration section. Further, change of the current value is made smooth in a transition from at least either the deceleration section or the acceleration section to the flat region or a transition from the flat region to at least either the deceleration section or the acceleration section. Accordingly, change of the current value of the deflection electromagnet 108 with respect to time is reduced to a range in which the current of the deflection electromagnet 108 can respond. Therefore, it is possible to prevent occurrence of a position jump and elimination of charged particles.

In addition, no smoothing region is provided in a reference signal according to the present embodiment, and thus no smoothing region is generated in a current signal corresponding to a region of accelerating charged particles and a region of decelerating charged particles. Accordingly, an acceleration cycle in the current signal can be made shorter than in a case where a smoothing region is provided in the reference signal in advance. As described above, the current signal generator 254 does not provide a flat region in which charged particles are placed in a stationary state at a predetermined energy in a case where irradiation to a patient is not performed, and provides the flat region in which the charged particles are placed in the stationary state at the predetermined energy in a case where irradiation of the charged particles to a patient is performed. Accordingly, it is possible to improve the processing efficiency of the entire particle-beam radiation treatment system 1, so that a treatment time can be made further shorter.

Figures 8, 9:
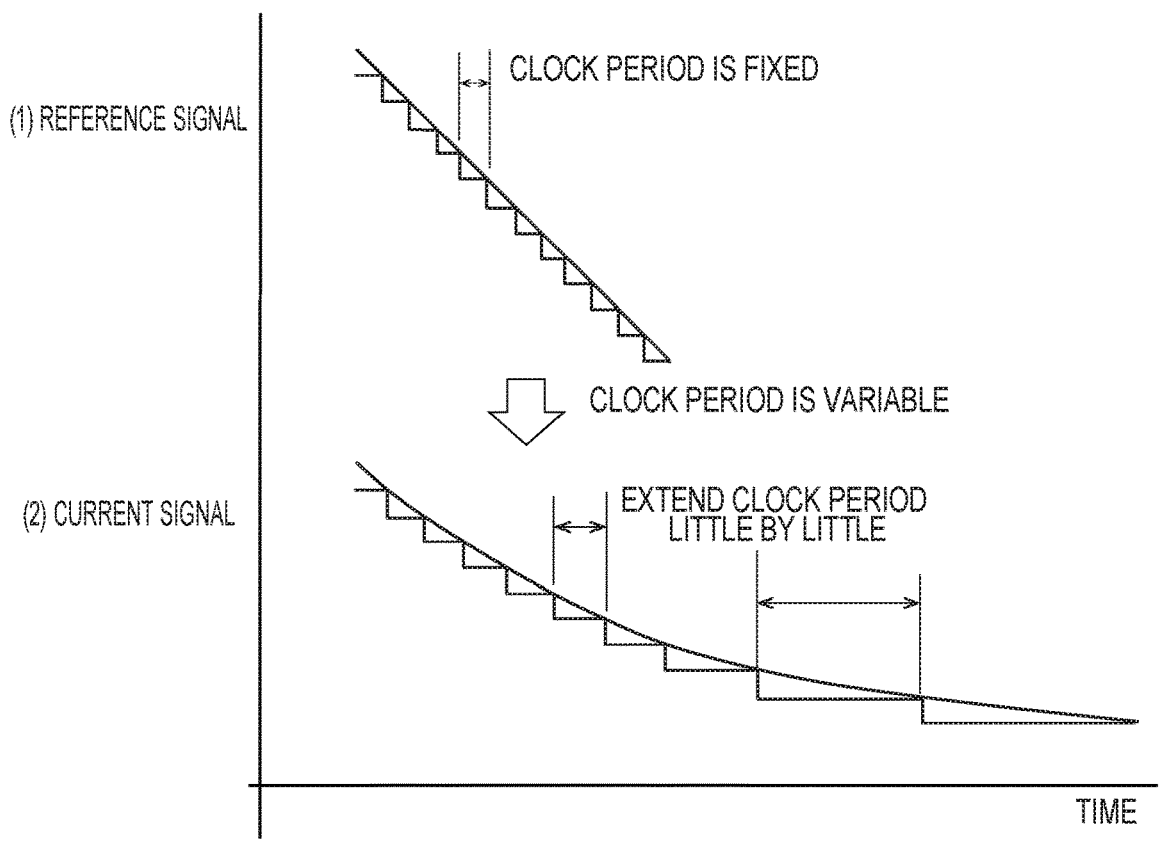
FIG. 8 is a diagram illustrating an example of generating a smoothing region from a reference signal in a time period in which charged particles are decelerated.
FIG. 9 is a diagram representing a relation between an energy stationary state and the number of clocks.

Next, an example of generating a smoothing region of a current signal from a reference signal in a time period in which charged particles are decelerated is described in more detail with reference to FIG. 8. FIG. 8 is a diagram illustrating an example of generating a smoothing region of a current signal from a reference signal in a time period in which charged particles are decelerated. The vertical axis represents the current signal and the horizontal axis represents a time. (1) illustrates a current signal in a case where the output period of a clock signal is fixed (that is, the reference signal is used as it is), and (2) illustrates a current signal in a case where the output period of the clock signal is continuously extended.

As illustrated in FIG. 8, when the period of the clock signal output by the second clock generator 216 (FIG. 1) is continuously increased, time change of an instruction value of an instruction signal output by the current signal generator 254 (FIG. 1) becomes gentle and a smoothing region is generated. To the contrary, when the period of the clock signal output by the second clock generator 216 is continuously shortened, time change of the instruction value of the current signal output by the current signal generator 254 (FIG. 1) becomes gentle and a smoothing region that makes smooth transition from a flat region to a linear deceleration region is generated.

It is desirable to set a time used for setting this smoothing region (a smoothing time) based on an energy for extracting charged particles. Further, in a case of changing an energy, that is, making change to an energy at which emission of charged particles is performed next, it is desirable to set the smoothing time to be longer as a current difference between the instruction values of the instruction signal corresponding to a difference between the energies before and after the change is larger. Here, the energy before energy change means a flat top in a case of first emission of charged particles in that acceleration cycle. In a case of second emission or later, the energy before energy change means an energy of previous emission of charged particles. When a width of energy change is larger, it is difficult for the energy of charged particles to follow change of the instruction signal. Therefore, by making a smoothing region gentler, it is possible to more surely prevent occurrence of a position jump and elimination of charged particles.

Next, information related to a clock signal used for control by the timing controller 210 according to the present embodiment is described with reference to FIGS. 9, 10, and 12. FIG. 9 is a diagram representing a relation among an energy stationary state of charged particles, the number of clocks when a clock is stopped, and the number of smoothing clocks required for generation of a smoothing region. The left column represents the number of the energy stationary state of charged particles, the middle column represents the number of clocks when the clock is stopped, and the right column represents the number of smoothing clocks.

The relation among the energy stationary state of charged particles, the number of clocks when the clock is stopped, and the number of smoothing clocks required for generation of a smoothing region illustrated in FIG. 9 is stored in the first memory 212 (FIG. 1) of the timing controller 210 in the form of a table.

As illustrated in FIG. 9, 1000 types of energy stationary states of charged particles are provided in the present embodiment. The number of clocks when the clock is stopped, and the number of smoothing clocks are associated with each of these 1000 types of energy stationary states of charged particles, respectively. For example, for an energy stationary state with the energy number 4, the second clock generator 216 stops the clock signal when the number of clocks reaches 1550 from output of a reset signal based on the table stored in the first memory 212. Further, when the number of clocks reaches 60 clocks before stop of the clock signal, that is, reaches 1550−60=1490, the second clock generator 216 changes an output mode of the clock signal from a fixed-period output mode to a variable-period output mode.

FIG. 10 is a diagram representing a relation between the number of clocks from start of smoothing and a clock interval. The left column represents the number of clocks from start of a smoothing process, that is, from start of change of the clock period in a transition to a variable-period output mode, and the middle column represents the clock interval in a case of the energy number 4. Although the number of smoothing clocks is 60 in FIG. 9, FIG. 10 represents the number of clocks up to 100 that is the maximum. The right column represents an example of other energy numbers as an energy number N. The relation between the number of clocks from start of smoothing and the clock interval illustrated in FIG. 10 is stored in the first memory 212 (FIG. 1) of the timing controller 21 in the form of a table.

Figure 11:
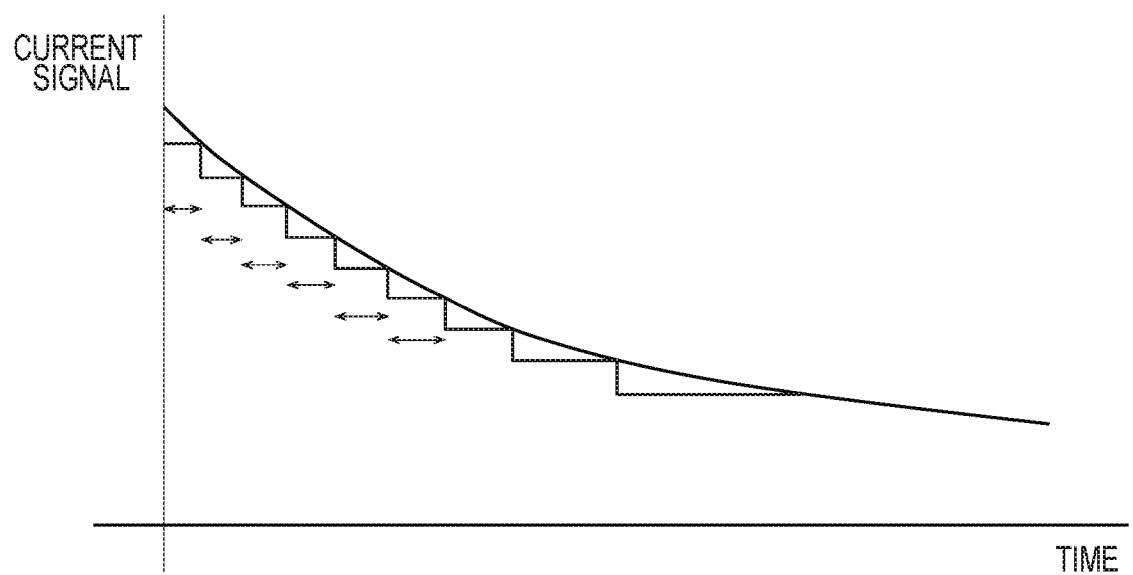
FIG. 11 is a diagram illustrating an example in which a smoothing region is generated in accordance with a variable period of a clock.

FIG. 11 is a diagram illustrating an example in which a smoothing region is generated in accordance with the clock interval for the energy number 4 in FIG. 10, that is, a variable period of a clock. The horizontal axis represents a time, and the vertical axis represents a current signal.

As illustrated in FIG. 11, the second clock generator 216 outputs a first clock signal 12 microseconds after start of smoothing, a second clock signal 16 microseconds after output of the first clock signal, and a third clock signal 22 microseconds after output of the second clock signal based on the table stored in the first memory 212 (FIG. 1). The current signal generator 254 (FIG. 1) outputs the reference signal (FIG. 7) stored in the third memory 252 as a current signal sequentially in response to these clock signals. By changing the period of the clock signal from start of smoothing in this manner, a smoothing region is generated in the current signal.

FIG. 12 is a diagram representing a relation between the number of clocks from start of smoothing and an elapsed time. The left column represents the number of clocks from start of smoothing, that is, from start of change of the clock period, and the middle column represents an elapsed time from start of smoothing in a case where an energy number is 4. Although the number of smoothing clocks is 60 in FIG. 9, FIG. 12 represents the number of clocks up to 100 that is the maximum. The right column represents an example of other energy numbers as an energy number N. FIG. 12 represents an equivalent content to that in FIG. 10 as a relation between the number of clocks from start of smoothing and an elapsed time. The relation between the number of clocks from start of smoothing and the elapsed time represented in FIG. 12 is stored in the first memory 212 (FIG. 1) of the timing controller 21 in the form of a table.

Figure 13:
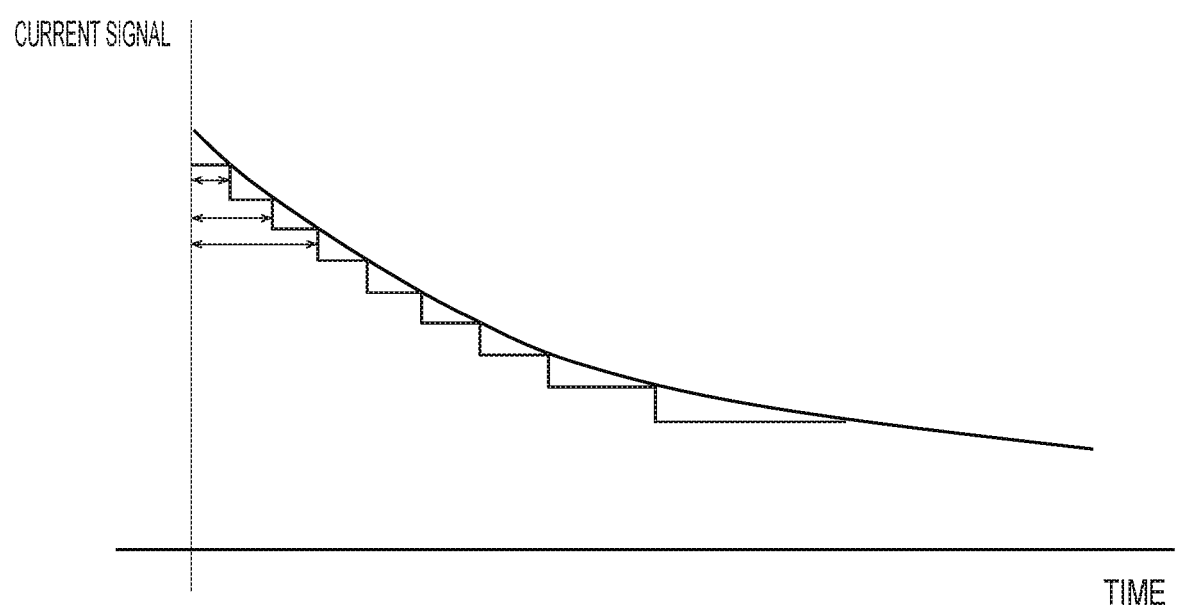
FIG. 13 is a diagram illustrating an example in which a smoothing region is generated in accordance with a period from start of smoothing.

FIG. 13 is a diagram illustrating an example in which a smoothing region is generated in accordance with a clock output time from start of smoothing, that is, the clock period, for the energy number 4 in FIG. 12. The horizontal axis represents a time, and the vertical axis represents a current signal.

As illustrated in FIG. 13, the second clock generator 216 outputs, for example, a first clock signal 12 microseconds after start of smoothing, a second clock signal 28 microseconds after start of smoothing, and a third clock signal 50 microseconds after start of smoothing based on the table stored in the first memory 212 (FIG. 1). The current signal generator 254 (FIG. 1) outputs the reference signal (FIG. 7) stored in the third memory 252 as the current signal sequentially in response to these clock signals. By changing the period of the clock signal from start of smoothing in this manner, a smoothing region can be generated in the current signal.

As described above, the first memory 212 of the timing controller 210 stores therein information related to clocks that is exemplified in FIGS. 9, 10, and 12, for example, in the form of a table. The second clock generator 216 outputs the clock signal to the power supply controller 252 based on a stationary energy number for which emission has been requested.

In the above example, a table is formed to define the number of clocks and a clock interval for each stationary energy. In another example, instead of setting the number of clocks and the clock interval for each set stationary energy, a table can also be set to define the number of clocks and the clock interval in accordance with a difference of instruction values of an instruction signal corresponding to a difference between stationary energies to which charged particles are to be changed. That is, in a case where charged particles are emitted at an energy number 100, for example, a table is defined in such a manner that the number of smoothing clocks and a clock interval in a transition to a flat region for the energy number 100 are different depending on an energy number for which previous emission of charged particles is performed.

The configuration of the table that achieves such definition is not limited. In a case where an energy difference between energy numbers is constant, for example, it suffices that the number of smoothing clocks and the clock interval are defined for each difference between energy numbers. For example, in a case where an energy number is changed from 1 to 101, the number of clocks and the clock interval that are associated with an energy difference of 100 in the table are referred to. By setting the number of clocks and the clock interval with respect to a difference between energy numbers, it is possible to achieve a smaller table than in a case where the number of clocks and the clock interval are set for all combinations of an energy number before change and an energy number after change. Here, an energy corresponding to a flat top may be registered in the table as an energy number 0, because the energy before change may be the flat top.

When the number of smoothing clocks and the clock interval are determined, a smoothing time is also determined. Therefore, the data table is also a table in which a stationary energy or a current difference corresponding to a difference between stationary energies and the smoothing time are associated with each other.

The timing controller 210 may calculate the period of a clock signal in accordance with the following expression. As illustrated in FIG. 7, it is necessary to increase the number of smoothing clocks with increase of a current difference that is a difference between instruction values of an instruction signal corresponding to a difference between stationary energies to which charged particles are to be changed.

Therefore, assuming that the number of smoothing clocks is Nmax, K1 is a given constant, and a current difference that is a difference between instruction values of an instruction signal corresponding to a difference between stationary energies is Dif, Expression 1 can be established, for example.

$$N\mathrm{max} = K1 \times \mathrm{Dif} \qquad \text{(Expression 1)}$$

Assuming that the n-th clock interval from start of smoothing is Tn, C1, C2, and C3 are given constants, and a current difference that is a difference between instruction values of an instruction signal corresponding to a difference between stationary energies is Dif, Expression 2 can be established.

$$Tn = C1 \times n \times \mathrm{Dif} \times \mathrm{Dif} + C2 \times n \times \mathrm{Dif} + C3 \times n \qquad \text{(Expression 2)}$$

Here, n is an integer from 0 to Nmax.

Further, the number of smoothing clocks Nmax can be represented in a general function form as Nmax=f(Dif). f( ) is a given linear function. Furthermore, a clock interval at the n-th smoothing from start of smoothing can also be represented in a general function form as T(n, Dif). T( ) is a given quadratic function. These functions may be defined in accordance with current characteristics of the deflection electromagnet 108 (FIG. 1) and the timing controller 210 may be caused to calculate the number of smoothing clocks and a smoothing time in real time.

The above expressions for obtaining the number of clocks and a clock interval used for setting a smoothing region are merely an example, and are not limited thereto. For example, a smoothing time used for setting a smoothing region may be calculated based on a current difference between instruction values of an instruction signal corresponding to a difference between stationary energies to which charged particles are to be changed, and then the number of clocks and a clock interval used for setting smoothing may be calculated based on this smoothing time. That is, although the smoothing time is determined by obtaining the number of clocks and the clock interval in the above example of expressions, the smoothing time may be calculated based on the current difference and then the number of clocks and the clock interval may be calculated based on the obtained smoothing time. Any calculation may be used, as long as the smoothing time is longer as the current difference is larger.

Further, a difference between stationary energies to which charged particles are changed is described. However, in a case of first emission of charged particles in an acceleration cycle, a current difference Dif is defined as a difference between instruction values of an instruction signal corresponding to a difference between the energy at the flat top and a stationary energy at which emission of the charged particles is performed. That is, a smoothing time is determined based on a current difference between energies of charged particles before and after energy change.

As described above, by obtaining the number of clocks and a clock interval used for setting a smoothing region by calculation in accordance with a difference between stationary energies to which charged particles are changed, it is possible to make a smoothing time longer as a difference between energies of charged particles before and after energy change is larger.

Figure 14:
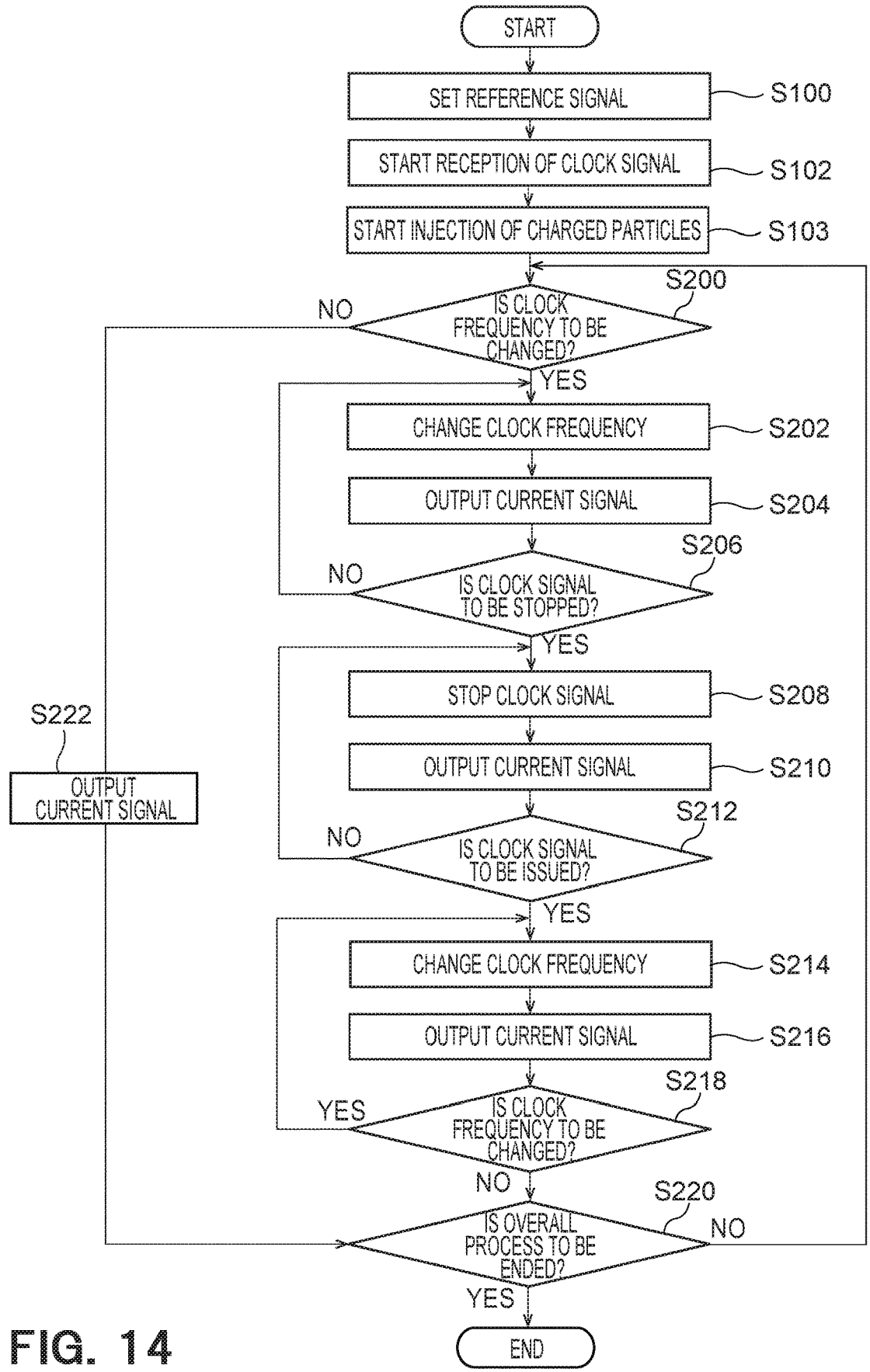
FIG. 14 is a flowchart for explaining generation of a current signal by using a variable clock signal.

FIG. 14 is a flowchart for explaining generation of a current signal by using a variable clock signal. An example of generating a current signal by using the reference signal exemplified in FIG. 6 is described here.

The computer system 50 sets a frequency reference signal and an amplitude reference signal that have been calculated and adjusted in advance in the second memory 242 of the high-frequency acceleration cavity controller 240 and sets a current reference signal in the third memory 252 of the power supply controller 250 (Step S100).

The second clock generator 216 starts outputting a clock signal and a reset signal upon reception of an output enable signal from the computer system 50. Alternatively, the second clock generator 216 outputs in advance the clock signal and the reset signal upon reception of an operation start signal for the computer system 50 (Step S102).

Next, the injector 102 injects charged particles into the main accelerator 104 in synchronization with the reset signal a fixed time after the reset signal (Step S103). Subsequently, the high-frequency acceleration cavity controller 240 outputs the frequency reference signal and the amplitude reference signal set in the second memory 242 to the high-frequency acceleration cavity 106 as a frequency signal and an amplitude signal sequentially in response to the clock signal. Similarly, the power supply controller 250 outputs the current reference signal set in the third memory 252 to the power supply 114 as a current signal sequentially in response to the clock signals. Accordingly, the charged particles are accelerated while revolving in a predetermined orbit in the main accelerator 104.

The timing controller 210 refers to a stop condition and a table that are set in the first memory 212 and determines whether to change the period of the clock signal (Step S200). The timing controller 210 refers to the stop condition and a table related to clocks (for example, information related to clocks illustrated in FIG. 9, 10, or 12) that are set in the first memory 212, and starts changing the period of the clock signal (Step S202) when the number of clocks is the number of clocks for starting smoothing associated with an energy number (YES in Step S200). The current signal generator 254 of the power supply controller 250 outputs the reference signal stored in the third memory 252 as the current signal sequentially in response to the clock signal. Accordingly, the smoothing region 510 is generated, as illustrated in FIG. 7, for example.

Next, the timing controller 210 refers to the stop condition and the table related to clocks that are set in the first memory 212, and determines whether to stop the clock signal (Step S204). In a case where the number of clocks is not the number of clocks that satisfies the stop condition (NO in Step S206), the timing controller 210 repeats the processes from Step S202.

Meanwhile, in a case where the number of clocks is the number of clocks that satisfies the stop condition (YES in Step S206), the timing controller 210 stops outputting the clock signal (Step S208). The current signal generator 254 continues to output the current signal at the time of stop of the clock signal to the power supply controller 250. Accordingly, a flat region that corresponds to a stationary state at the first energy is generated, as illustrated in FIG. 7, for example.

Next, the timing controller 210 determines whether to resume output of the clock signal (Step S212). The timing controller 210 determines that stop of the clock signal is continued (NO in Step S212) when it has not received an irradiation end signal or an irradiation request signal at a different energy from the irradiation control device 42, and repeats the processes from Step S208.

Meanwhile, the timing controller 210 determines that output of the clock signal is to be resumed when it has received the irradiation end signal or the irradiation request signal at a different energy from the irradiation control device 42 (YES in Step S212). Subsequently, the timing controller 210 starts changing the period of clock signal (Step S214).

Next, the timing controller 210 refers to the stop condition and the table that are set in the first memory 212 and determines whether to stop changing the period of clock signal (Step S218). In a case where the number of clocks is not the number of clocks that corresponds to stopping of the changing (YES in Step S218), the processes from Step S214 are repeated. The current signal generator 254 outputs the reference signal stored in the third memory as the current signal sequentially in response to the clock signal. Accordingly, the smoothing region 512 is generated as illustrated in FIG. 7, for example.

Meanwhile, in a case where the number of clocks is the number of clocks that corresponds to stopping of the changing (NO in Step S218), the timing controller 210 determines whether to end the whole processing (Step S220). When it is determined that the whole processing is not to be ended (NO in Step S220), the processes from Step S200 are repeated.

In a case where the number of clocks is not the number of clocks for starting smoothing associated with the energy number (NO in Step S200), the timing controller 210 outputs the clock signal having the fixed period to the power supply controller 250. The current signal generator 254 of the power supply controller 250 outputs the current reference signal set in the third memory 252 to the power supply 114 as the current signal sequentially in response to the clock signal (Step S222). Meanwhile, when the whole processing is to be ended (YES in Step S220), the whole control processing is ended. The timing controller 210 continuously changes the period of a clock signal to generate the smoothing region in this manner.

As described above, according to the present embodiment, the current signal generator 254 is configured to continuously change the period of a clock signal before stopping the clock signal, in a case where the current signal generator 254 outputs a reference signal as a time-series current signal in response to reception of the clock signal. Accordingly, change of an instruction value of a time-series instruction signal with respect to time is made smooth and thus the current signal generator 254 can output the current signal in which a smoothing region is formed from the reference signal in which no smoothing region is provided.

Further, in actual treatment, it is unnecessary to provide a flat region that makes a current value of the deflection electromagnet 108 constant at a beam energy at which extraction of charged particles is not performed, and it is possible to provide the flat region at a beam energy at which extraction of charged particles is actually performed. Accordingly, a cycle of accelerating charged particles can be further shortened, which contributes to shortening of a time for treating a patient. In particular, in a case where the types of energies for extracting charged particles achieved by an accelerator are increased (for example, to 600 types) as compared with the types conventionally achieved, the acceleration cycle cannot become longer because of increase of the types. Therefore, it is possible to use the types of irradiation energies that are about the same number as or more than the number of the conventionally achieved types without using hardware such as a range shifter, thus contributing to shortening of a treatment time.

Furthermore, it is possible to make a smoothing time longer as a difference between energies of charged particles before and after energy change is larger.

Second Embodiment

The particle-beam radiation treatment system 1 according to a second embodiment is different from the system 1 according to the first embodiment in generating a smoothing region in a current signal by using a current correction signal, in place of generating the smoothing region in the current signal by changing the frequency of a clock signal of the second clock generator 216. In the following descriptions, differences between the second embodiment and the first embodiment are described.

Figure 15:
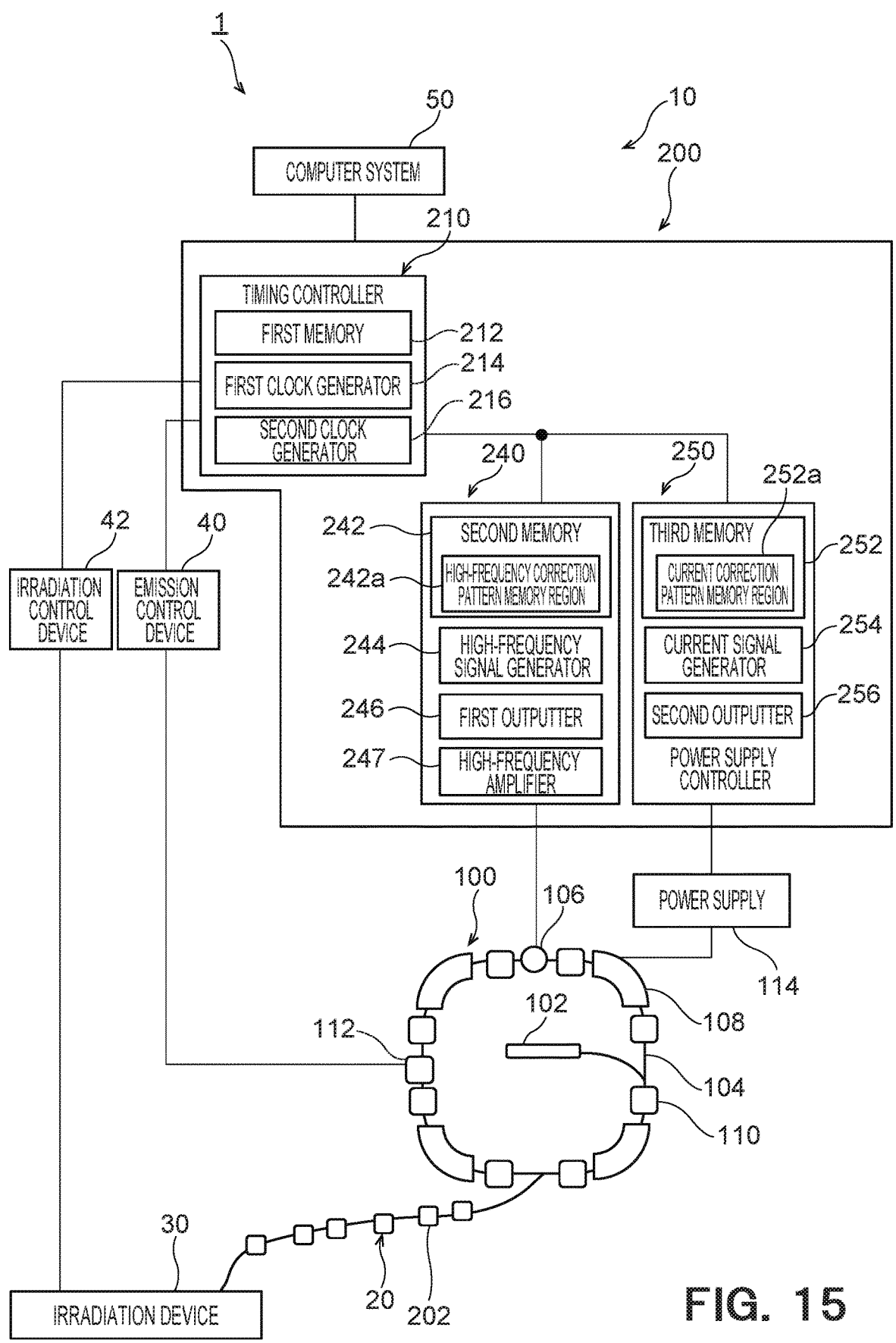
FIG. 15 is a diagram illustrating a schematic overall configuration of a particle-beam radiation treatment system according to a second embodiment.

FIG. 15 is a diagram illustrating a schematic overall configuration of the particle-beam radiation treatment system 1 according to the second embodiment. As illustrated in FIG. 15, this configuration is different from that in the second embodiment in that a high-frequency correction pattern memory region 242a is provided in the second memory 242 and a current correction pattern memory region 252a is provided in the third memory 252. A frequency correction signal and an amplitude correction signal that correct a frequency reference signal and an amplitude reference signal, respectively, are stored in the high-frequency correction pattern memory region 242a. Further, a correction signal that corrects a current reference signal is stored in the current correction pattern memory region 252a.

Figure 16:
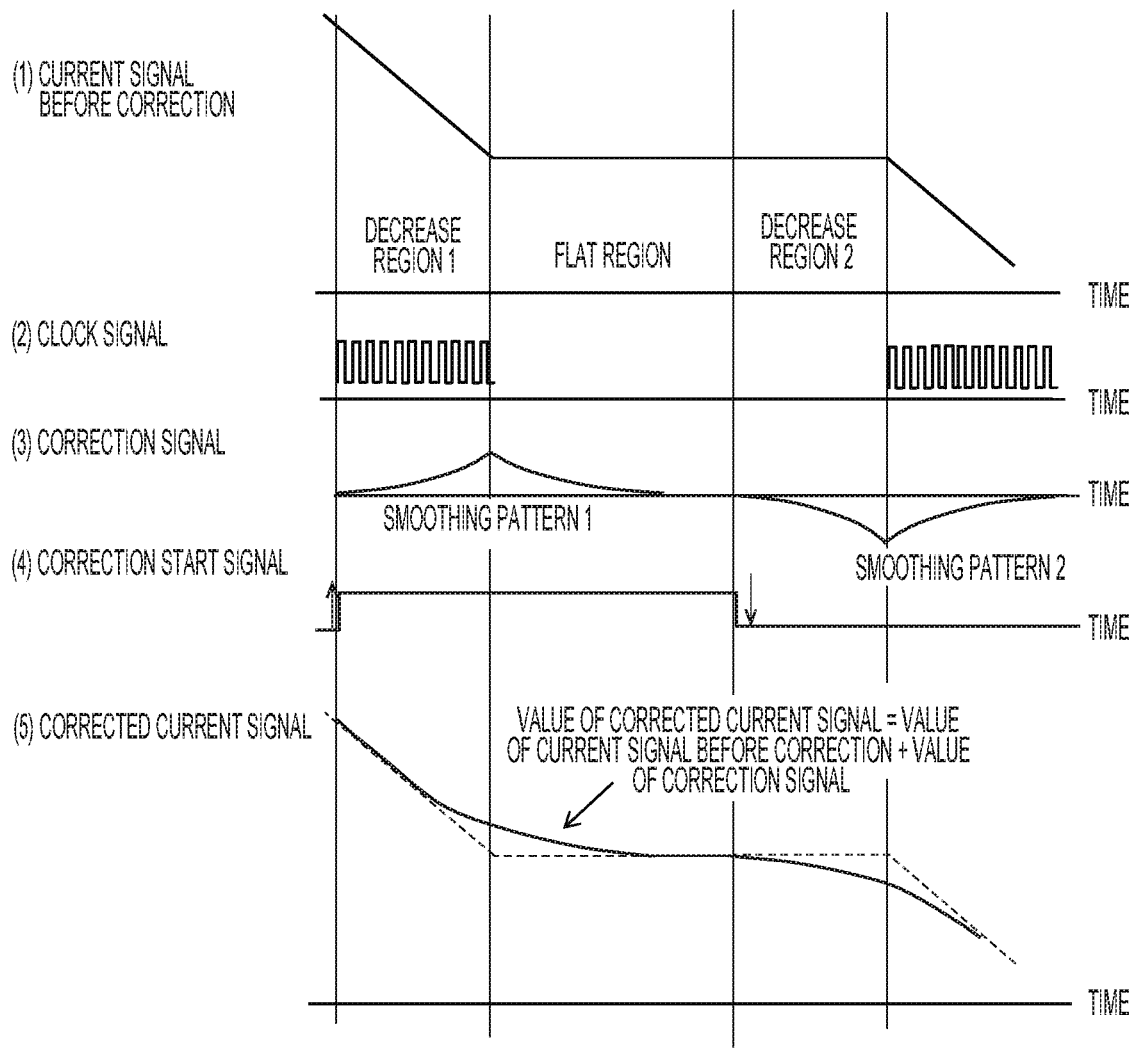
FIG. 16 is a diagram representing a relation between a current signal before correction, generated based on a reference signal, and a correction signal.

FIG. 16 is a diagram representing a relation between a current signal before correction, generated based on a reference signal, and a correction signal. The horizontal axis represents a time, and the vertical axis represents the current signal before correction in (1), a clock signal in (2), the correction signal in (3), a correction start signal in (4), and a corrected current signal in (5). An example of processing by the timing controller 210 and processing by the power supply controller 250 according to the present embodiment in a case where a smoothing process is performed is described with reference to FIG. 16.

First, the current signal before correction output by the current signal generator 254 is described. As illustrated in FIG. 16 as a decrease region 1 and a decrease region 2, for example, the current signal generator 254 outputs the current reference signal stored in the third memory 252 as the current signal before correction sequentially in response to reception of the clock signal. Further, when the clock signal is stopped as illustrated as a flat region, for example, the current signal generator 254 continues to output the reference signal at the time of stop of the clock signal as the current signal.

Next, the correction signal used for correcting the current signal by the current signal generator 254 is described. An instruction value of the correction signal (a smoothing pattern 1 or 2, for example) has been calculated in advance in such a manner that it smoothly changes with respect to time when an instruction value of the current signal before correction and the instruction value of the correction signal are added to each other. Therefore, when the instruction value of the instruction signal before correction and the instruction value of the correction signal are added to each other, the instruction value of the instruction signal which changes smoothly with respect to time is obtained. That is, an instruction value of the corrected current signal is made smooth, and a derivative with respect to time continuously changes.

The current signal generator 254 generates, based on the correction start signal, the corrected current signal that has the instruction value obtained by adding the instruction value of the instruction signal before correction and the instruction value of the correction signal to each other. In more detail, in a transition from the decrease region 1 to the flat region corresponding to an energy stationary state of charged particles, for example, the current signal generator 254 generates the corrected current signal that has the instruction value obtained by adding the instruction value of the instruction signal before correction and the instruction value of the correction signal (the smoothing pattern 1) to each other based on detection of a rising signal of the correction start signal. Further, in a transition from the flat region corresponding to the energy stationary state of charged particles to the decrease region 2, for example, the current signal generator 254 generates the corrected current signal that has the instruction value obtained by adding the instruction value of the current signal before correction and the instruction value of the correction signal (the smoothing pattern 2) to each other based on detection of a falling signal of the correction start signal.

In the decrease regions 1 and 2, for example, the extent of change of the instruction value of the instruction signal before correction with respect time is maintained to a predetermined value. Therefore, as illustrated in FIG. 16, the smoothing pattern 1 that indicates a time-series value of the correction signal added at rising of the correction start signal and the smoothing pattern 2 that indicates the time-series value of the correction signal added at falling of the correction start signal have a relation in which positive and negative are inverted. Accordingly, the smoothing process by the correction start signal can be performed both in the transition from the decrease region 1 to the flat region and the transition from the flat region to the decrease region 2.

Further, the current signal generator 254 may generate the current signal by adding a value obtained by multiplying the instruction value of the correction signal (for example, the smoothing pattern 1 or 2) by a coefficient that is in accordance with a difference between current values respectively corresponding to stationary energies, to the instruction value of the reference signal. Accordingly, it is possible to adjust the amount of smoothing with respect to the magnitude between stationary energies. In particular, as described in the first embodiment, it is possible to achieve the correction signal that provides a longer smoothing time as a difference between energies of charged particles before and after energy change is larger.

Next, the correction start signal output by the timing controller 210 is described. The timing controller 210 outputs the correction start signal to the power supply controller 250 before stopping the clock signal based on a clock stop condition received from the computer system 50. Further, upon reception of an irradiation stop signal or an irradiation request signal at a different energy from the irradiation control device 42, the timing controller 210 causes the correction start signal to fall. The timing controller 210 then resumes output of the clock signal after a predetermined number of clocks has elapsed. The timing controller 210 stops the clock signal after a predetermined number of clocks has elapsed from output of the correction start signal in this manner. Further, the timing controller 210 resumes output of the clock signal after a predetermined number of clocks has elapsed from stop of output of the correction start signal.

As is understood from the above descriptions, when the instruction value of the instruction signal before correction and the instruction value of the correction signal are added to each other, the current signal that changes smoothly with respect to time, that is, the current signal of which the extent of change with respect to time is smaller than a predetermined value is obtained.

Figure 17:
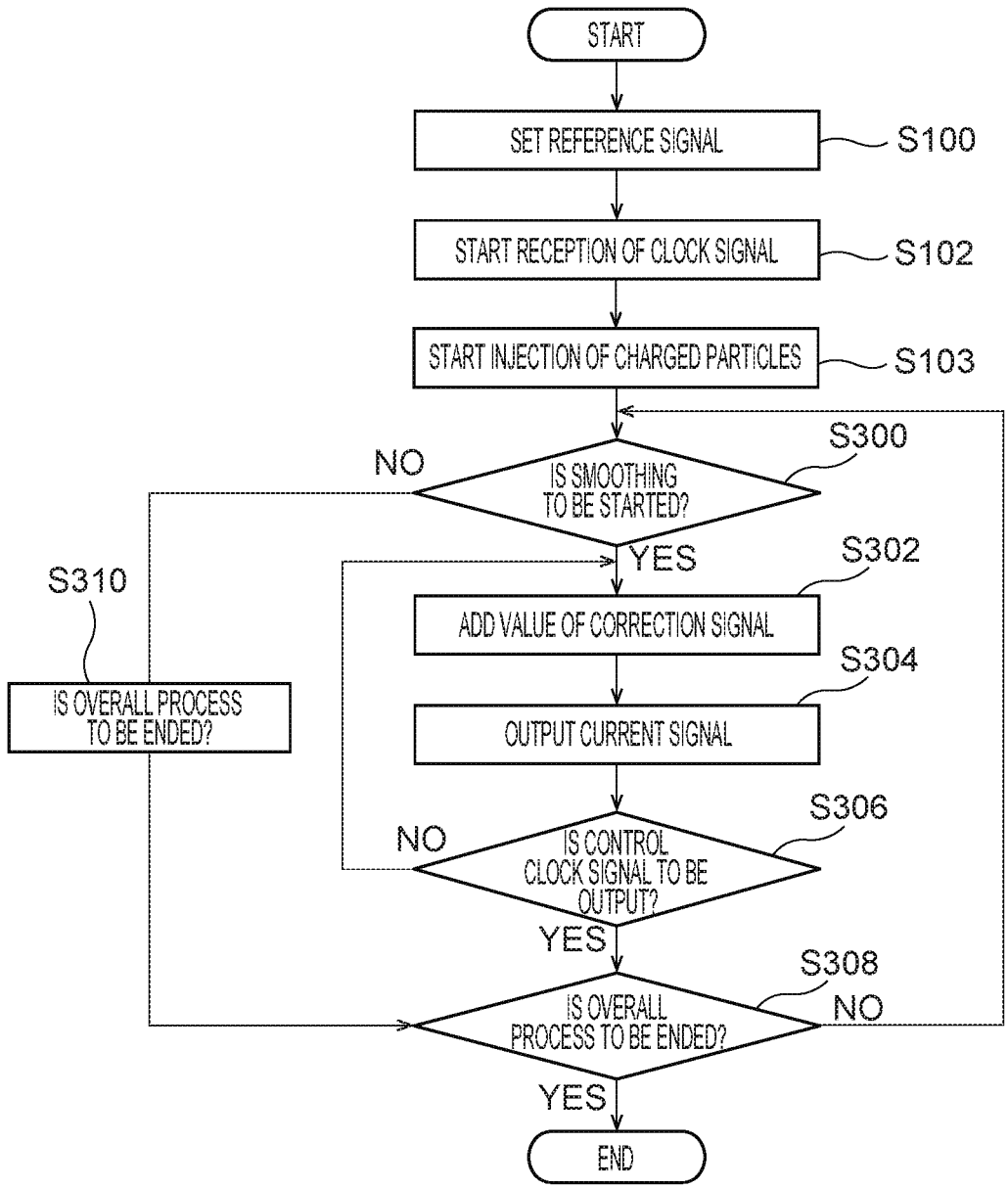
FIG. 17 is a flowchart for explaining generation of a current signal by using a correction signal.

FIG. 17 is a flowchart for explaining generation of a current signal by using a correction signal. Processes equivalent to those in the first embodiment are denoted by like numerals and the descriptions thereof are omitted. An example of generating a current signal is described here.

First, the timing controller 210 continues to output a fixed-period clock signal to the current signal generator 254 also after injection of charged particles into the main accelerator 104. The current signal generator 254 outputs a reference signal as a current signal before correction sequentially in response to reception of the clock signal.

Next, the timing controller 210 refers to a stop condition set in the first memory 212 and determines whether to start smoothing using a correction signal (Step S300). When determining that smoothing is to be started (YES in Step S300), the timing controller 210 outputs a correction start signal to the power supply controller 250. The current signal generator 254 of the power supply controller 250 outputs a current signal to which an instruction value that is the sum of an instruction value of the reference signal and an instruction value of the correction signal (for example, the smoothing pattern 1) is added based on detection of a rising signal of the correction start signal (Step S304). Further, when a predetermined number of clocks has elapsed from a time of start of output of the correction start signal, the timing controller 210 stops the clock signal. Subsequently, the current signal generator 254 outputs the current signal obtained by adding the reference signal at the time of stop of the clock and the correction signal to each other. Furthermore, when a predetermined number of clocks has elapsed, the current signal generator 254 outputs the reference signal at the time of stop of the clock as the current signal.

Next, the timing controller 210 determines whether to resume output of the clock signal (Step S306). The timing controller 210 determines that stop of the clock signal is continued (NO in Step S306) when it has not received an irradiation end signal or an irradiation request signal at a different energy from the irradiation control device 42, and repeats the processes from Step S302.

Meanwhile, when the timing controller 210 has received the irradiation end signal or the irradiation request signal at a different energy from the irradiation control device 42, it determines that output of the clock signal is to be resumed (YES in Step S306), stops outputting the correction start signal, and resumes output of the clock signal after a predetermined number of clocks has elapsed. Upon detection of a falling signal of the correction start signal, the current signal generator 254 of the power supply controller 250 outputs the current signal to which an instruction value obtained by adding the instruction value of the reference signal and the instruction value of the correction signal (for example, the smoothing pattern 2) to each other is added. Furthermore, when a predetermined number of clocks has elapsed, the current signal generator 254 outputs the reference signal as the current signal sequentially.

Next, the timing controller 210 determines whether to end the whole processing (Step S308). When it is determined that the whole processing is not to be ended (NO in Step S308), the processes from Step S300 are repeated.

Meanwhile, when determining that smoothing is not to be started (NO in Step S300), the timing controller 210 continues to output the clock signal having the fixed period to the power supply controller 250. The power supply controller 250 outputs the current reference signal set in the third memory 252 as the current signal sequentially in response to the clock signal (Step S310). Meanwhile, when the whole control processing is to be ended (YES in Step S308), the whole processing is ended. The timing controller 210 generates a smoothing region by adding an instruction value of an instruction signal and the instruction value of the correction signal that reduces change of the instruction value of the instruction signal to each other in this manner.

As described above, according to the present embodiment, the current signal generator 254 is configured to add, to an instruction value of a time-series instruction signal, an instruction value of a correction signal that reduces change of the instruction value with respect to time before and after stop of a clock signal. Accordingly, change of the instruction value with respect to time is made smooth and thus a position jump and elimination of charged particles are avoided.

Further, in a case of an acceleration cycle not involving emission of charged particles to the beam transport system 20, a flat region that makes a current value of the deflection electromagnet 108 constant to correspond to a predetermined energy for extracting the charged particles is not provided. In a case of an acceleration cycle involving emission of charged particles to the beam transport system 20, the flat region is provided. Accordingly, the cycle of accelerating charged particles can be further shortened, and a time for treating a patient can be further shortened.

At least a part of the control device 200 described in the above embodiments may be constituted by hardware or software. When the device is constituted by software, it is possible to configure that a program for realizing at least a part of the functions of the control device 600 is held in a recording medium such as a flexible disk or a CD-ROM and a computer is caused to read and execute the program. The recording medium is not limited to a detachable one such as a magnetic disk or an optical disk, and a stationary recording medium such as a hard disk device or a memory may also be applicable.

Further, the program for realizing at least a part of the functions of the control device 200 may be distributed via a communication line such as the Internet (including wireless communication). Further, the program in an encoded, modulated, or compressed state may be distributed via a wired line or a wireless line such as the Internet, or stored in a recording medium and distributed.

While certain embodiments have been described, these embodiments have been presented by way of example only, and are not intended to limit the scope of the inventions. Indeed, the novel embodiments described herein may be embodied in a variety of other forms and various omissions, substitutions, and changes may be made without departing from the spirit of the inventions. The embodiments and their modifications are intended to be included in the scope and the spirit of the invention and also in the scope of the invention and their equivalents described in the claims.

The invention claimed is:

1. A control method for an accelerator including a plurality of deflection electromagnets configured to generate a magnetic field that causes charged particles to revolve in a main accelerator in accordance with an acceleration energy of the charged particles and a power supply configured to supply a current that generates the magnetic field to the deflection electromagnets based on a current-value instruction signal, the method comprising:
provided a flat region that makes a current value of the deflection electromagnet constant to correspond to a predetermined energy for extracting the charged particles in the current-value instruction signal in a case of an acceleration cycle involving emission of the charged particles to a beam transport system;
not providing the flat region in the current-value instruction signal in a case of an acceleration cycle not involving emission of the charged particles to the beam transport system;
smoothing time change of a current value of the deflection electromagnet in a transition of the current value to the flat region or a transition from the flat region; and
determining a time required for the smoothing based on a predetermined energy for extracting the charged particles or a difference between energies before and after change to the predetermined extraction energy.

2. A control method for an accelerator including an injector configured to accelerate charged particles to an injection energy and inject the charged particles into a main accelerator, a high-frequency acceleration cavity configured to give an acceleration energy to the charged particles injected into the main accelerator, a plurality of deflection electromagnets configured to generate a magnetic field that causes the charged particles to revolve in the main accelerator in accordance with the acceleration energy of the charged particles, a power supply configured to supply a current that generates the magnetic field to the deflection electromagnets based on a current-value instruction signal, and an emission device for causing the charged particles to be emitted from the main accelerator to a beam transport system, the method comprising:
generating a flat bottom section corresponding to a lowest energy of the charged particles, a top point or a flat top section corresponding to a highest energy, an acceleration section for acceleration from the flat bottom section, and a deceleration section for deceleration from the top point or the flat top section to the flat bottom in time change of a current value of the deflection electromagnet in an acceleration cycle not involving emission of the charged particles to the beam transport system, and not generating a flat region that makes the current value of the deflection electromagnet constant to correspond to a predetermined extraction energy;
generating, in time change of the current value of the deflection electromagnet in an acceleration cycle involving emission of the charged particles to the beam transport system, the flat region in which the current value is constant to correspond to a predetermined extraction energy in a middle of a section corresponding to at least either the deceleration section or the acceleration section; and
smoothing the time change of the current value in a transition from the corresponding section to the flat region or a transition from the flat region to the corresponding section, and determining a time required for the smoothing based on a predetermined energy for extracting the charged particles or a difference between energies before and after change to the predetermined extraction energy.

3. A control device for an accelerator including a plurality of deflection electromagnets configured to generate a magnetic field that causes charged particles to revolve in a main accelerator in accordance with an acceleration energy of the charged particles and a power supply configured to supply a current that generates the magnetic field to the deflection electromagnets based on a current-value instruction signal, comprising a current signal generator configured to
generate the current-value instruction signal provided with a flat region that makes a current value of the deflection electromagnet constant to correspond to a predetermined energy for extracting the charged particles in a case of an acceleration cycle involving emission of the charged particles to a beam transport system, and
generate the current-value instruction signal not provided with the flat region in a case of an acceleration cycle not involving emission of the charged particles to the beam transport system, wherein
the current-value instruction signal includes a smoothing section in which current change is made smooth in a transition of the current value of the deflection electromagnet to the flat region or a transition from the flat region, and
a length of time of the smoothing section is determined based on a predetermined energy for extracting the charged particles or a difference between energies before and after change to the predetermined extraction energy.

4. The device of claim 3 further comprising:
a clock signal generator configured to generate a clock signal; and
a memory configured to store therein a time-series reference signal that is associated with the clock signal and has information on a current value, wherein
the current signal generator outputs the time-series reference signal sequentially to generate the current-value instruction signal in response to reception of the clock signal, and generates the smoothing section in accordance with continuous increase or decrease of a clock period.

5. The device of claim 4, wherein
the memory stores therein a data table in which a predetermined energy for extracting the charged particles or a difference between energies before and after change to the predetermined extraction energy and a length of time of the smoothing section are associated with each other, and
the clock signal generator outputs the clock signal based on the data table.

6. The device of claim 4, wherein the clock signal generator outputs the clock signal by using at least either a first expression that calculates number of clocks used for setting the smoothing section based on the difference between the energies before and after the change to the predetermined extraction energy or a second expression that calculates a clock period corresponding to the number of clocks from a time at which setting of the smoothing section is started.

7. The device of claim 4, wherein the clock signal is synchronized with a current signal of a quadrupole electromagnet of the main accelerator and a frequency instruction signal of a high-frequency acceleration cavity of the main accelerator.

8. The device of claim 3, further comprising a memory configured to store therein a time-series reference signal that includes information on a time-series current value used as a reference and a time-series correction signal corresponding to a smoothing region for limiting a current flowing in the deflection electromagnet within a changeable range per unit time, wherein the current signal generator generates the current-value instruction signal that smoothes the current change based on the time-series reference signal and the time-series correction signal.

9. The device of claim 8, wherein the current signal generator generates the current-value instruction signal based on a value obtained by adding an instruction value of the reference signal and an instruction value of the correction signal to each other.

10. The device of claim 9, wherein the current signal generator generates the current-value instruction signal by adding a value obtained by multiplying the instruction value of the correction signal by a coefficient corresponding to the difference between the energies before and after the change to the predetermined extraction energy to the instruction value of the reference signal.

11. The device of claim 3, wherein the smoothing section that smoothes the current change is calculated based on transient characteristics of the deflection electromagnet.

12. A particle-beam radiation treatment system comprising:

an injector configured to accelerate charged particles to an injection energy and inject the charged particles to a main accelerator;

a high-frequency acceleration cavity configured to give an acceleration energy to the charged particles injected into the main accelerator;

a plurality of deflection electromagnets configured to generate a magnetic field that causes the charged particles to revolve in the main accelerator in accordance with the acceleration energy of the charged particles;

a power supply configured to supply a current that generates the magnetic field to the deflection electromagnets based on a current-value instruction signal;

an emission device for causing the charged particles to be emitted from the main accelerator to a beam transport system; and a control device configured to control at least the power supply among the injector, the high-frequency acceleration cavity, the power supply, and the emission device, wherein the control device includes a current signal generator configured to generate the current-value instruction signal provided with a flat region that makes a current value of the deflection electromagnet constant to correspond to a predetermined energy for extracting the charged particles in a case of an acceleration cycle involving emission of the charged particles to the beam transport system, generate the current-value instruction signal not provided with the flat region in a case of an acceleration cycle not involving emission of the charged particles to the beam transport system, generate a smoothing section that smoothes current change in a transition to the flat region or a transition from the flat region, and determine a length of time of the smoothing section based on a predetermined energy for extracting the charged particles or a difference between energies before and after change to the predetermined extraction energy.

13. The particle-beam radiation treatment system of claim 12 further comprising:

a clock signal generator configured to generate a clock signal; and a memory configured to store therein a time-series reference signal that is associated with the clock signal and has information on a current value, wherein the current signal generator outputs the time-series reference signal sequentially to generate the current-value instruction signal in response to reception of the clock signal, and generates the smoothing section in accordance with continuous increase or decrease of a clock period.

14. The particle-beam radiation treatment system of claim 13, wherein the memory stores therein a data table in which a predetermined energy for extracting the charged particles or a difference between energies before and after change to the predetermined extraction energy and a length of time of the smoothing section are associated with each other, and the clock signal generator outputs the clock signal based on the data table.

15. The particle-beam radiation treatment system of claim 13, wherein the clock signal generator outputs the clock signal by using at least either a first expression that calculates number of clocks used for setting the smoothing section based on the difference between the energies before and after the change to the predetermined extraction energy or a second expression that calculates a clock period corresponding to the number of clocks from a time at which setting of the smoothing section is started.

16. The particle-beam radiation treatment system of claim 13, wherein the clock signal is synchronized with a current signal of a quadrupole electromagnet of the main accelerator and a frequency instruction signal of a high-frequency acceleration cavity of the main accelerator.

17. The particle-beam radiation treatment system of claim 12, further comprising a memory configured to store therein a time-series reference signal that includes information on a time-series current value used as a reference and a time-series correction signal corresponding to a smoothing region for limiting a current flowing in the deflection electromagnet within a changeable range per unit time, wherein the current signal generator generates the current-value instruction signal that smoothes the current change based on the time-series reference signal and the time-series correction signal.

18. The particle-beam radiation treatment system of claim 17, wherein the current signal generator generates the current-value instruction signal based on a value obtained by adding an instruction value of the reference signal and an instruction value of the correction signal to each other.

19. The particle-beam radiation treatment system of claim 18, wherein the current signal generator generates the current-value instruction signal by adding a value obtained by multiplying the instruction value of the correction signal by a coefficient corresponding to the difference between the energies before and after the change to the predetermined extraction energy to the instruction value of the reference signal.

20. The particle-beam radiation treatment system of claim 12, wherein the smoothing section that smoothes the current change is calculated based on transient characteristics of the deflection electromagnet.

* * * * *